(12) United States Patent
Ludwig et al.

(10) Patent No.: US 9,594,019 B1
(45) Date of Patent: Mar. 14, 2017

(54) OPTICAL TOMOGRAPHY FOR MICROSCOPY, CELL CYTOMETRY, MICROPLATE ARRAY INSTRUMENTATION, CRYSTALLOGRAPHY, AND OTHER APPLICATIONS

(71) Applicant: Lester F. Ludwig, San Antonio, TX (US)

(72) Inventors: Lester F. Ludwig, San Antonio, TX (US); Karen Hao, Arlington, MA (US); Frank Hu, San Francisco, CA (US); Alice Huang, Belle Mead, NJ (US); Pooncharas Tipgunlakant, San Francisco, CA (US)

(73) Assignee: Lester F. Ludwig, San Antonio, TX (US)

( * ) Notice: Subject to any disclaimer, the term of this patent is extended or adjusted under 35 U.S.C. 154(b) by 0 days.

(21) Appl. No.: 13/963,931

(22) Filed: Aug. 9, 2013

(51) Int. Cl.
G01N 21/59 (2006.01)

(52) U.S. Cl.
CPC .................................. *G01N 21/59* (2013.01)

(58) Field of Classification Search
CPC ........................................................ G01N 21/59
USPC .......................................................... 356/432
See application file for complete search history.

(56) References Cited

U.S. PATENT DOCUMENTS 8,068,227 B2 * 11/2011 Tormod ........................ 356/442

* cited by examiner

*Primary Examiner* — Roy M Punnoose
(74) *Attorney, Agent, or Firm* — Procopio, Cory, Hargreaves & Savitch LLP

(57) ABSTRACT

An optical tomography system including a light emitting array having one or more light emitting diodes (LEDs), a sample holding module and a light sensing array comprising one or more light emitting diodes (LEDs), wherein the light sensing array is configured to sense light emitted from the light emitting array, which has passed through the sample holding module.

18 Claims, 44 Drawing Sheets

Light Sensing**

Light Sensing**

Light Emitting**

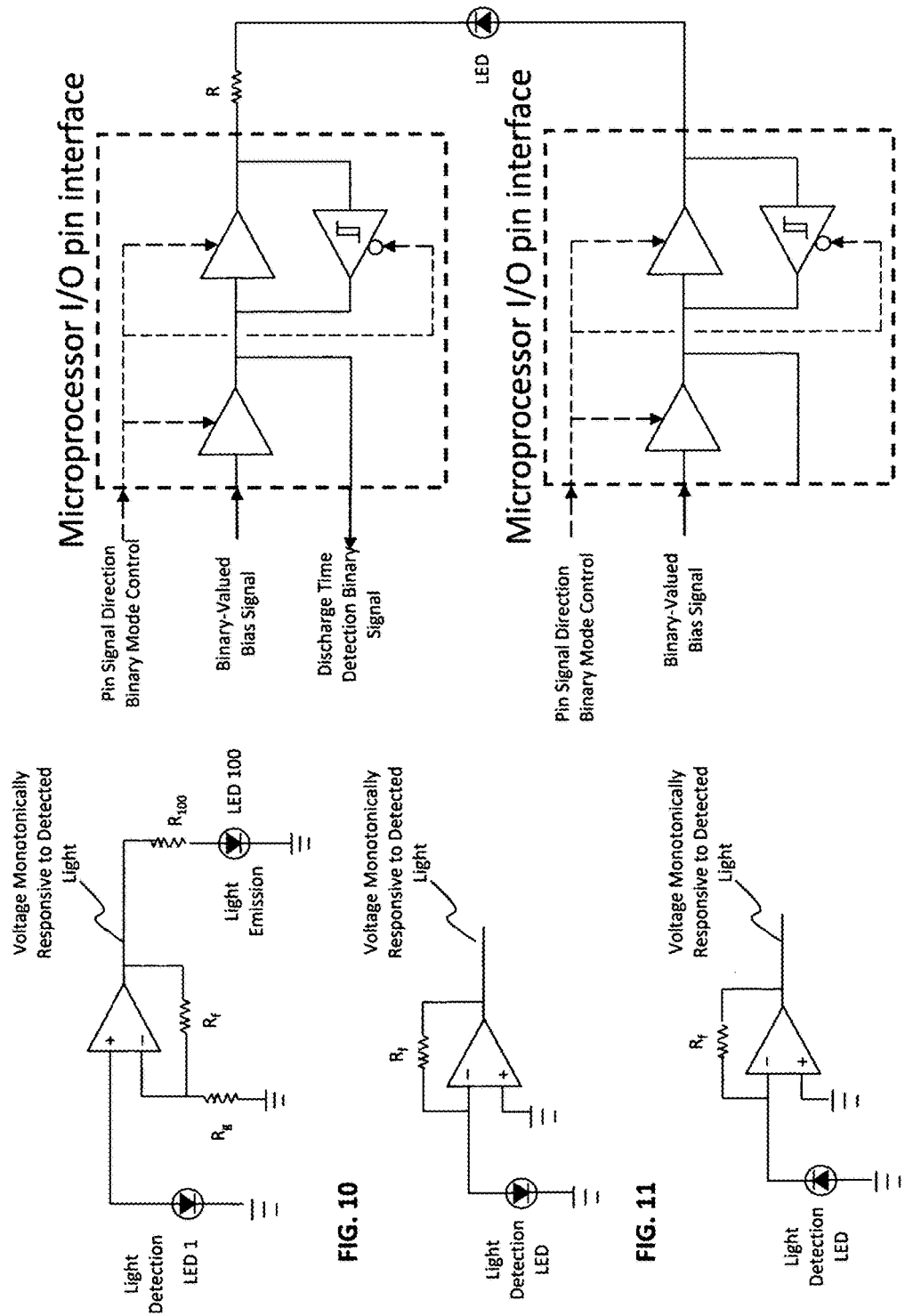

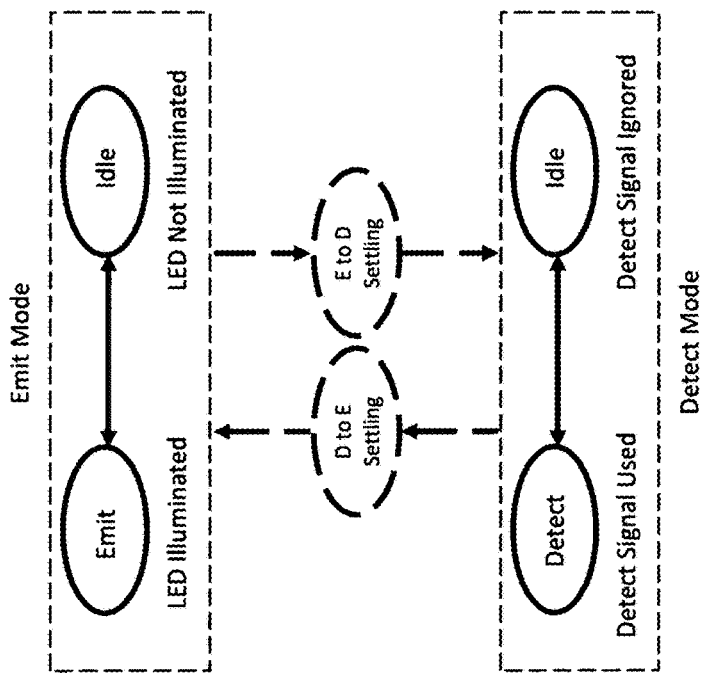
FIG. 20
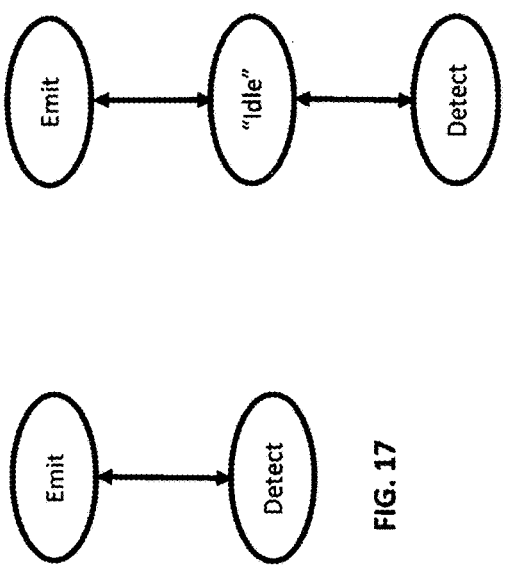
FIG. 18
FIG. 17
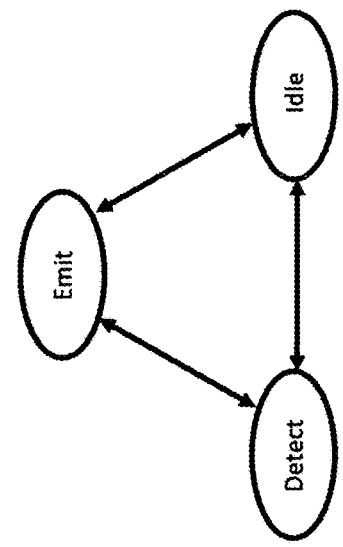
FIG. 19

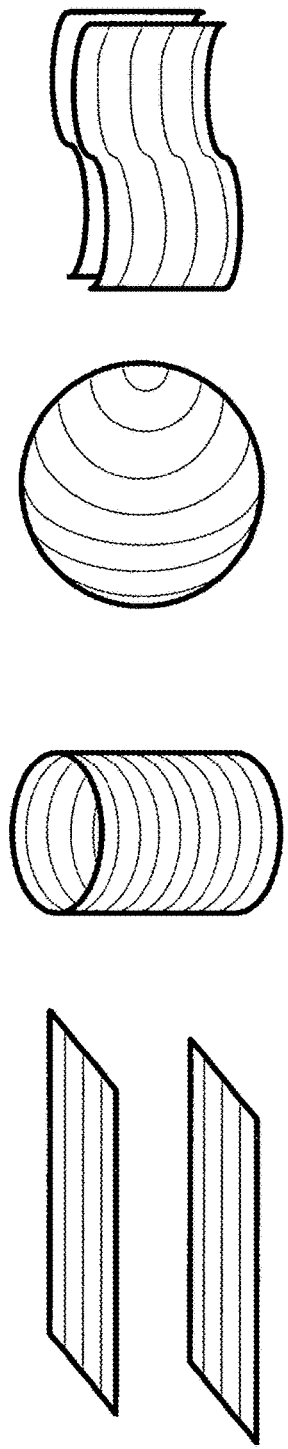
FIG. 21d
FIG. 21c
FIG. 21b
FIG. 21a
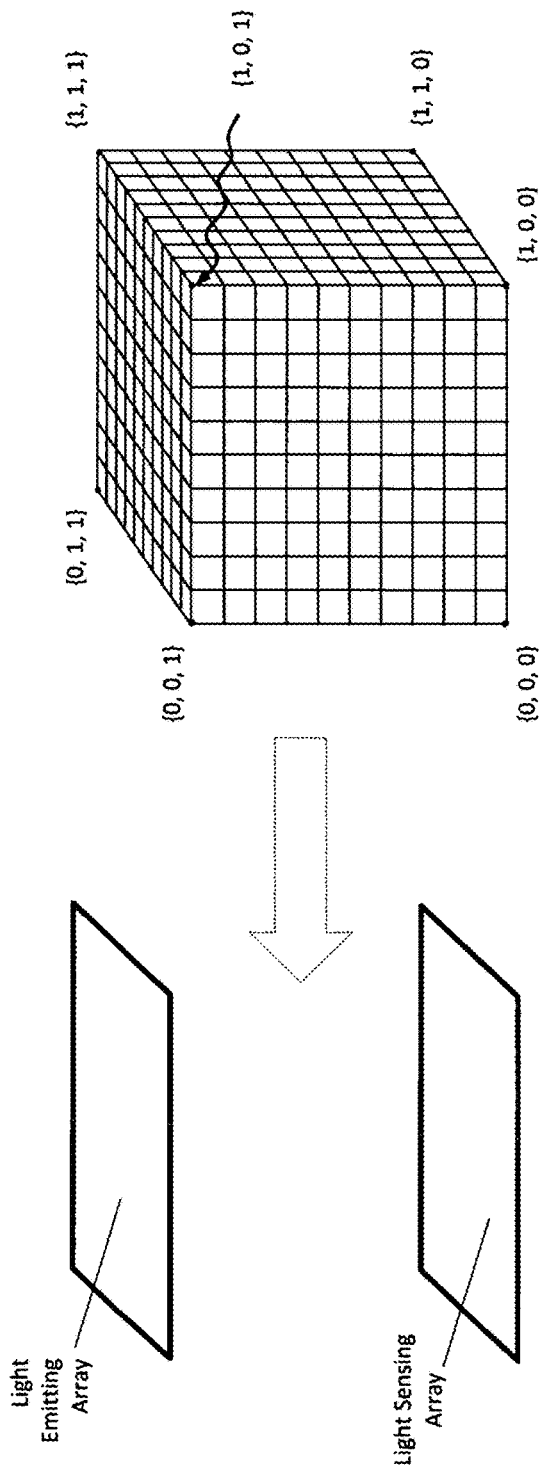
FIG. 22

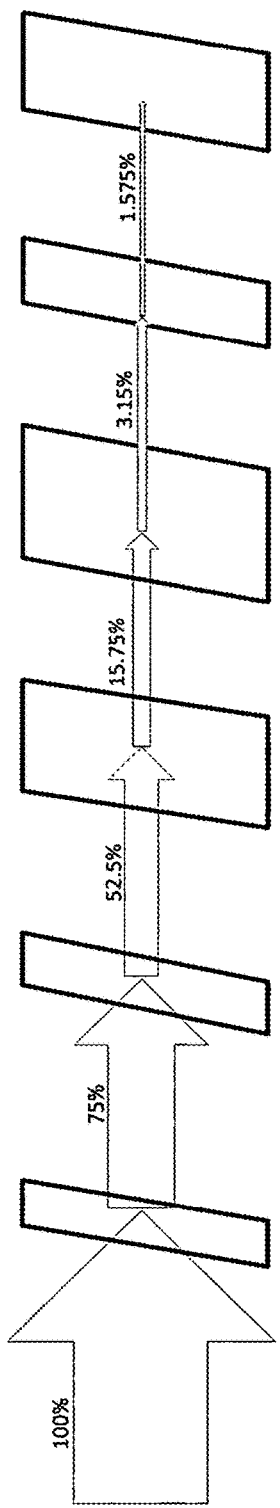

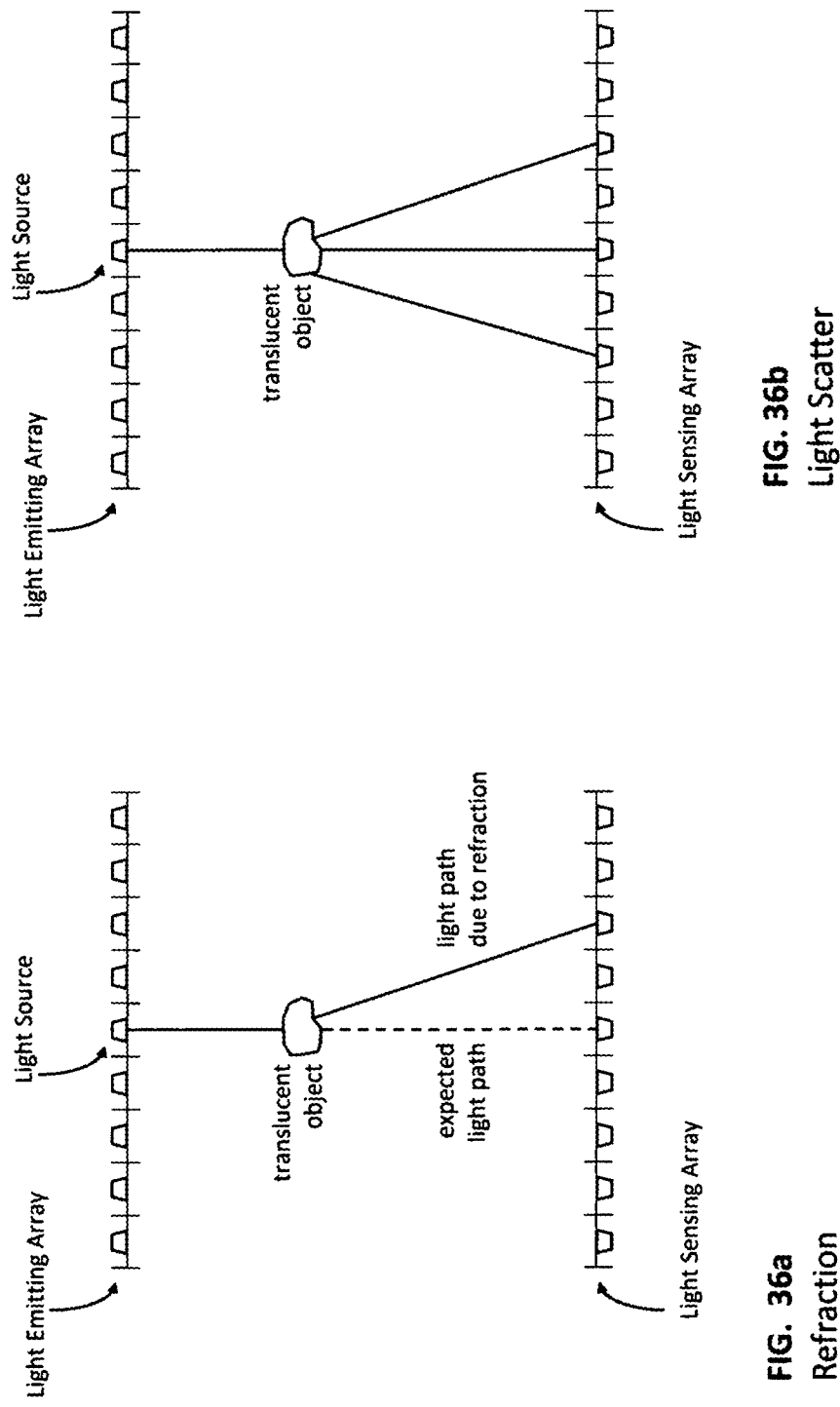

Reflection

Adapted from: Cappelli, Raffaele; Ferrara, Matteo; Maltoni, Davide. "Minutia Cylinder-Code: A New Representation and Matching Technique for Fingerprint Recognition." IEEE Transactions on Pattern Analysis and Machine Intelligence. December 2010 (Vol. 32 No. 12). Pp 2128-2141.

Discretized cylinder at three different angles

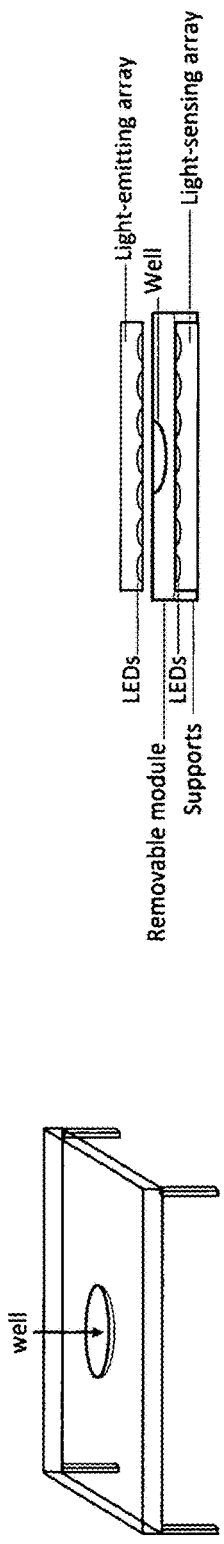
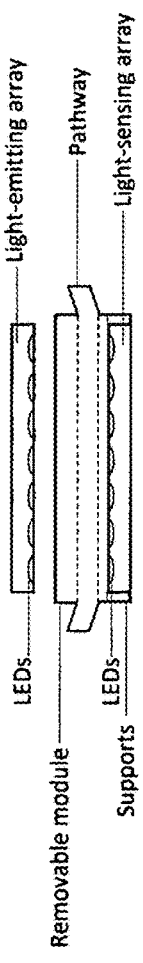
FIG. 42a
FIG. 42b
FIG. 43a
FIG. 43b

OPTICAL TOMOGRAPHY FOR MICROSCOPY, CELL CYTOMETRY, MICROPLATE ARRAY INSTRUMENTATION, CRYSTALLOGRAPHY, AND OTHER APPLICATIONS

COPYRIGHT & TRADEMARK NOTICES

A portion of the disclosure of this patent document may contain material, which is subject to copyright protection. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND OF THE INVENTION

Field of the Invention

The present invention pertains to tomography and 3D imaging, and more specifically to optical tomography for microscopy, cell cytometry, microplate array instrumentation, and other applications.

Overview of the Invention

Tomography refers to computational imaging by sections or sectioning via the use of any kind of penetrating wave, such as x-rays, gamma rays, radio-frequency waves, light, etc. as can be produced by electron-positron annihilation, electrons, ions, magnetic particles, light source, etc. Optical tomography is a form of computed tomography that creates a digital volumetric model of an object by reconstructing images made from light transmitted and scattered through an object. Optical tomography relies on the object under study being at least partially optically transparent. The present invention presents applications and opportunities in optical tomography which have remained largely unexplored and undeveloped. Light emitting diodes, or LEDs, have both light emitting and sensing properties. With the abundance of high and low performance LEDs at an economical price, leveraging the properties of LEDS, organic LEDs (OLEDs), etc., provides an important reason to consider such an invention. For example, OLEDs arrays are already in wide use in many types of electronic displays and they can be fabricated via printed electronics on a variety of surfaces such as glass, mylar, plastics, paper, etc. Leveraging some of the properties of such materials, LED arrays can be readily bent, printed on curved surfaces, etc. Such properties create vast opportunities for 3-D imaging in areas such as microscopy, cell cytometry, microplate array instrumentation, and other applications.

BRIEF DESCRIPTION OF THE DRAWINGS

The above and other aspects, features and advantages of the present invention will become more apparent upon consideration of the following description of preferred embodiments taken in conjunction with the accompanying drawing figures, wherein:

FIGS. 10-13 depict various example circuits demonstrating various exemple approaches to detecting light with an LED.

FIGS. 17-20 depict example state diagrams for the operation of the LED and the use of input signals and output signals.

FIGS. 21a-21d shows example geometries of light emitting and light sensing arrangements for various optical tomography systems.

FIG. 22 shows an example embodiment of a discretized space between a planar light emitting and light sensing arrangement in an optical tomography system.

FIG. 27a depicts an example cascade of non-uniform light loss transmission through objects of different thicknesses.

FIG. 27b depicts an example set of data based on FIG. 27a showing a relationship between transmittance and percentage of light loss.

FIG. 36a depicts an example of refraction of a light path transmitted through a transparent object between light emitting and light sensing arrangement.

FIG. 36b depicts an example of light scattering of a light path transmitted through a translucent object between light emitting and light sensing arrangement.

FIGS. 40a-40b show an example embodiment of a discretization of space for a cylindrical light emitting and light sensing arrangement in an optical tomography system, wherein FIG. 40b shows increased discretization.

FIG. 42a illustrates an example sample holding module, as a slide with a well for a planar light emitting and light sensing arrangement in an optical tomography system for cytometry.

FIG. 42b illustrates a side view of the example holding module of FIG. 42a.

FIG. 43a illustrates an example holding module, as a pathway for a planar light emitting and light sensing arrangement in an optical tomography system.

FIG. 43b illustrates a side view of the example holding module of FIG. 43a.

FIG. 44b illustrates a side view of the example holding module of FIG. 44a.

FIG. 52b illustrates a side view of FIG. 52a.

DETAILED DESCRIPTION

In the following description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention.

In the following description, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

1. Light Sourcing and Light Sensing

Figure 1:
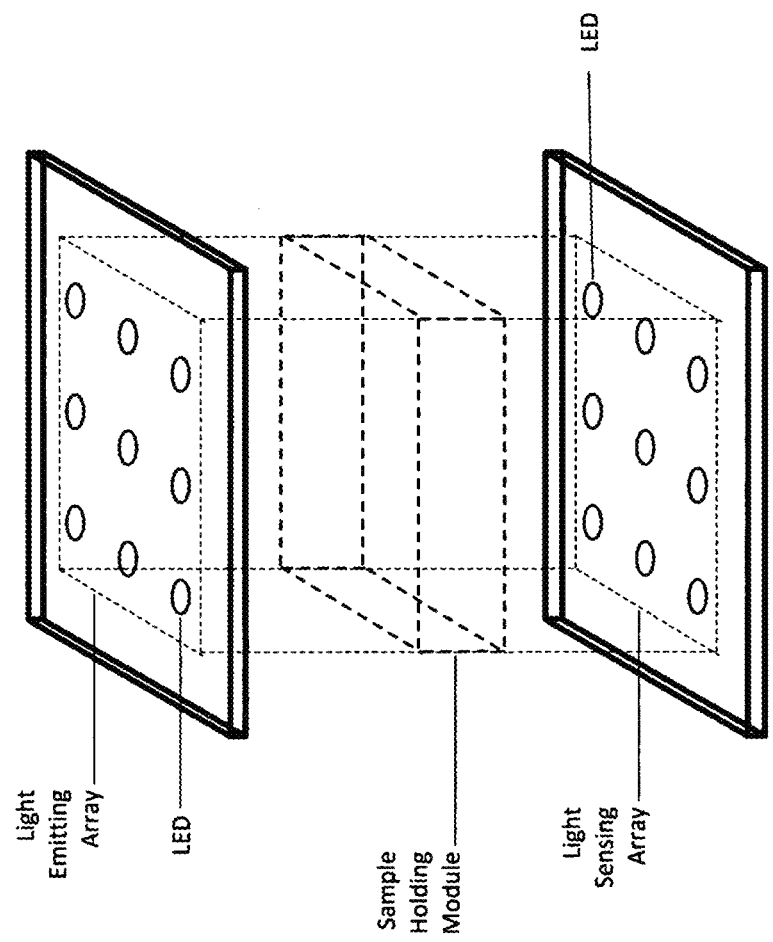
FIG. 1 shows an example embodiment of a planar light emitting and light sensing arrangement in an optical tomography system.

FIG. 1 shows an example embodiment of a planar light emitting and light sensing arrangement in an optical tomography system, depicting various elements of the system such as light emitting and light sensing arrays, each comprised of LEDs, and a holding module. FIG. 1 is illustrative in its depiction of an embodiment of the present invention but not restrictive.

Light sourcing or emitting and light sensing arrangements of the present invention can be an array of light emitting (light emitter) or light sensing (light sensor) elements. In an example embodiment, as shown in FIG. 1, a planar 2-dimensional light sensing or light sensor array and a planar 2-dimensional light emitting or light emission array face each other in a parallel arrangement configured so each sensor in the light sensor plane can receive light emitted by at least one light emitter or light emitting element in the light emitter plane. In a planar arrangement, the light emitting and light sensing arrays have n by n or $n^2$ LEDs and there will be at most $n^4$ light paths because each light path is defined by a pairing of light emitting and light sensing LEDs and there are $n^2 \times n^2 = n^4$ possible pairings of light emitting to light sensing LEDs. The quantity and arrangement of light emitting and light sensing elements can vary depending on the geometric arrangement.

1.1 Light Sourcing and Light Sensing Technologies

Light emitting and light sensing elements can comprise light-emitting diodes (LEDs), thin-film/printed organic light-emitting diodes (OLEDs), thin-film/printed organic light-emitting transistors (OLETs), etc. In various implementations the resolutions and spatial layout of the array of light-emitting elements can match, exceed, or be less than that of the image sensor pixel array as can be advantageous for reasons of function, cost, performance, etc. Further, the high-density array of light-emitting elements can comprise light-emitting elements of various wavelengths as can be advantageous in producing traditional optical color images and/or special scientific images, i.e., ultraviolet LEDs. It is also noted that LEDs behave as (wavelength sensitive) photodiodes. Thus, an LED array can be used as an image sensing array. Additionally, individual elements in an LED array can be switched between inactive (or idle) mode, light-emitting mode, and light-sensing mode.

Figure 2:
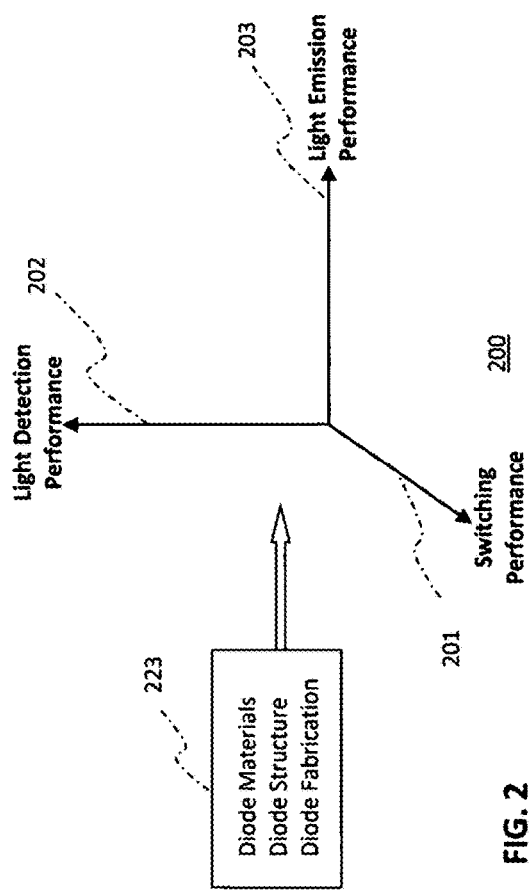
FIG. 2 depicts an optimization space for semiconductor diodes comprising attributes of signal switching performance, light emitting performance, and light detection performance.
Figure 3:
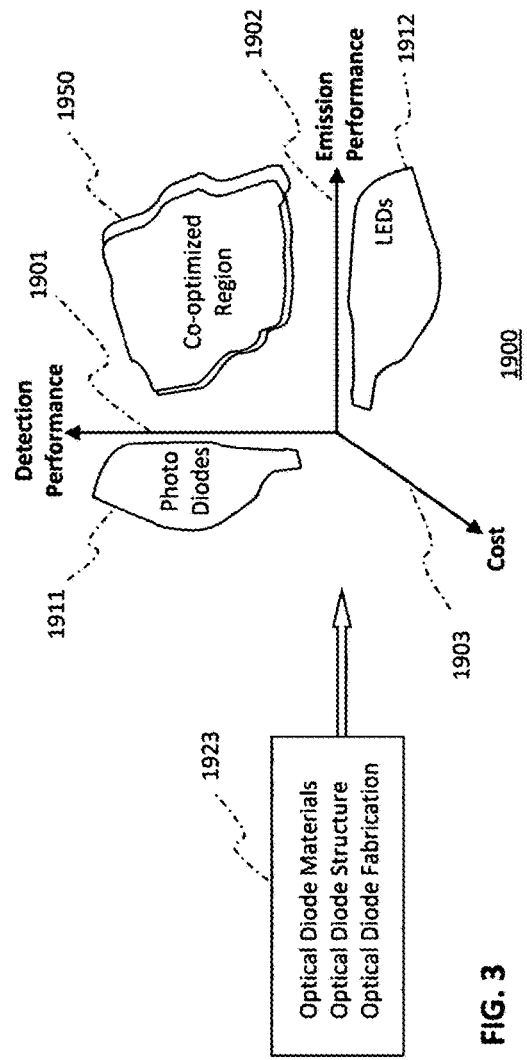
FIG. 3 depicts an example metric space representation of device realizations for optoelectronic devices and regions of optimization and co-optimization.

Such an arrangement, if used as an image sensor, can be sequentially operated to produce reflected-light contact imaging. In an implementation, the illuminating LED array is used both as a sequentially scanned light source and, via sequencing and/or multiplexing, as a reflective-imaging light sensor. High resolution sensors or organic light sensors that are not LEDs especially in planar geometry arrangement can also be implemented in certain embodiments of the present invention. In some embodiments, LEDs with both emitting and sensing properties require co-optimizing of both sets of properties. In other embodiments, LEDs with strictly emitting properties or LEDs with strictly detecting properties might be advantageous to optimize performance. For example, as illustrated in pending U.S. patent application Ser. No. 13/180,345, FIG. 2 depicts an optimization space for semiconductor diodes comprising attributes of signal switching performance, light emitting performance, and light detection performance. Specific diode materials, diode structure, and diode fabrication approaches can be adjusted to optimize a resultant diode for switching function performance (for example, via use of abrupt junctions), light detection performance such as via a P-I-N structure comprising a layer of intrinsic semiconducting material between regions of n-type and p-type material, or light detection performance. FIG. 3 depicts an example metric space representation of device realizations for optoelectronic devices and regions of optimization and co-optimization. Specific optoelectrical diode materials, structure, and fabrication approaches can be adjusted to optimize a resultant optoelectrical diode for light detection performance such as via a P-I-N structure comprising a layer of intrinsic semiconducting material between regions of n-type and p-type material versus light emission performance versus cost Optimization within the plane defined by light detection performance and cost traditionally result in photodiodes while optimization within the plane defined by light emission performance and cost traditionally result in LEDs. Specific optoelectrical diode materials, structure, and fabrication approaches can be adjusted to co-optimize an optoelectrical diode for both good light detection performance and light emission performance versus cost. A resulting co-optimized optoelectrical diode can be used for multiplexed light emission and light detection modes. These permit a number of applications of the present invention.

Figure 4C:
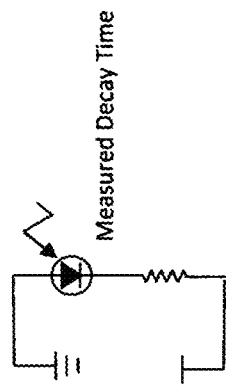
FIG. 4c shows an example schematic diagram of a light-sensing LED arrangement for measuring decay time.
Figure 4B:
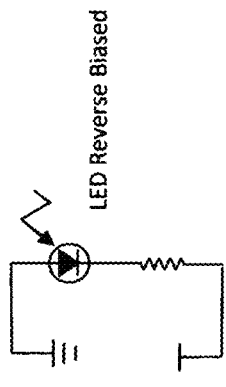
FIG. 4b shows an example schematic diagram of a light-sensing LED in a reverse-bias arrangement.
Figure 4A:
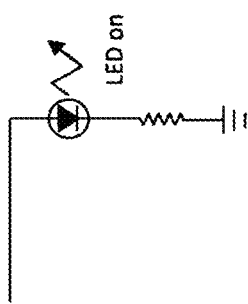
FIG. 4a shows an example schematic diagram of a light-emitting LED arrangement.

FIG. 4a shows an example schematic diagram of a light-emitting LED arrangement. In contrast to FIG. 4a, FIG. 4b shows an example schematic diagram of a light-sensing LED in a reverse-bias arrangement. FIG. 4c shows an example schematic diagram of a light-sensing LED arrangement for measuring decay time. Pending U.S. patent application Ser. No. 13/180,345 explains how light sensing is typically performed by photosite CCD (charge-coupled device) elements, phototransistors, CMOS photodetectors, and photodiodes. Photodiodes are often viewed as the simplest and most primitive of these, and typically comprise a PIN (P-type/Intrinsic/N-type) junction rather than the more abrupt PIN (P-type/N-type) junction of conventional signal and rectifying diodes. However, virtually all diodes are capable of photoelectric properties to some extent. In particular, LEDs, which are diodes that have been structured and doped specific types of optimized light emission, can also behave as (at least low-to moderate performance) photodiodes. Each LED in an array of LEDs can be alternately used as a photodetector or as a light emitter. At any one time, each individual LED would be in one of three states, a light emission mode, a light detection mode, or an inactive (or idle) mode as can be advantageous for various operating strategies. The state transitions of each LED can be coordinated in a wide variety of ways to afford various multiplexing, signal distribution, and signal gathering schemes as can be advantageous.

1.2 Multiplexing

A variety of methods can be implemented for the multiplexing circuitry for LED arrays utilized in the present invention. As illustrated in pending U.S. patent application Ser. No. 13/180,345, for rectangular arrays of LEDs, it is typically useful to interconnect each LED with access wiring arranged to be part of a corresponding matrix wiring arrangement. The matrix wiring arrangement is time-division multiplexed. Such time-division multiplexed arrangements can be used for delivering voltages and currents to selectively illuminate each individual LED at a specific intensity level (including very low or zero values so as to not illuminate).

Figure 5:
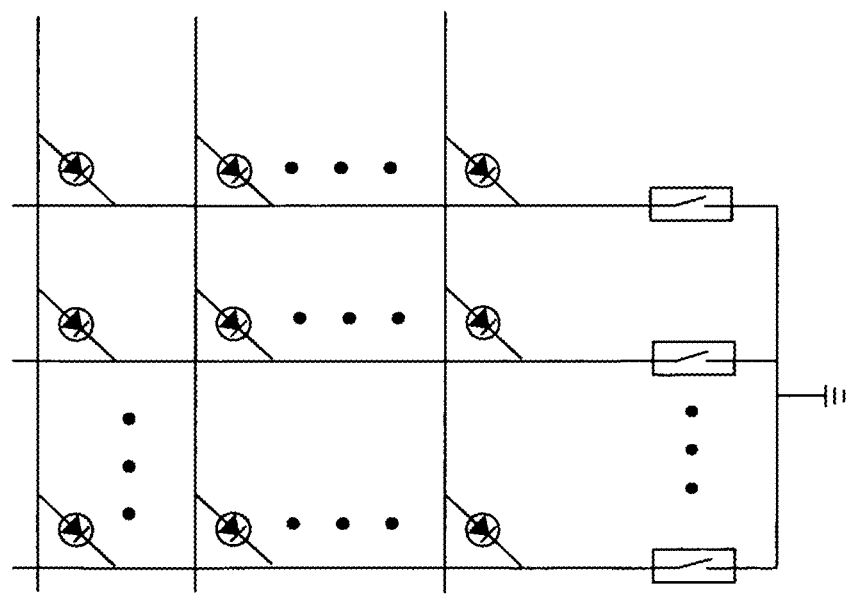
FIG. 5 depicts an example multiplexing arrangement for a two-dimensional array of LEDs.

An example multiplexing arrangement for a two-dimensional array of LEDs is depicted in FIG. 5. Here each of a plurality of normally-open analog switches are sequentially closed for brief disjointed intervals of time. This allows the selection of a particular subset (here, a column) of LEDs to be grounded while leaving all other LEDs in the array not connected to ground. Each of the horizontal lines then can be used to connect to exactly one grounded LED at a time. The plurality of normally-open analog switches in FIG. 5 can be controlled by an address decoder so that the selected subset can be associated with a unique binary address, as suggested in FIG. 6. The combination of the plurality of normally-open analog switches together with the address decoder form an analog line selector. By connecting the line decoder's address decoder input to a counter, the columns of the LED array can be sequentially scanned.

Figure 6:
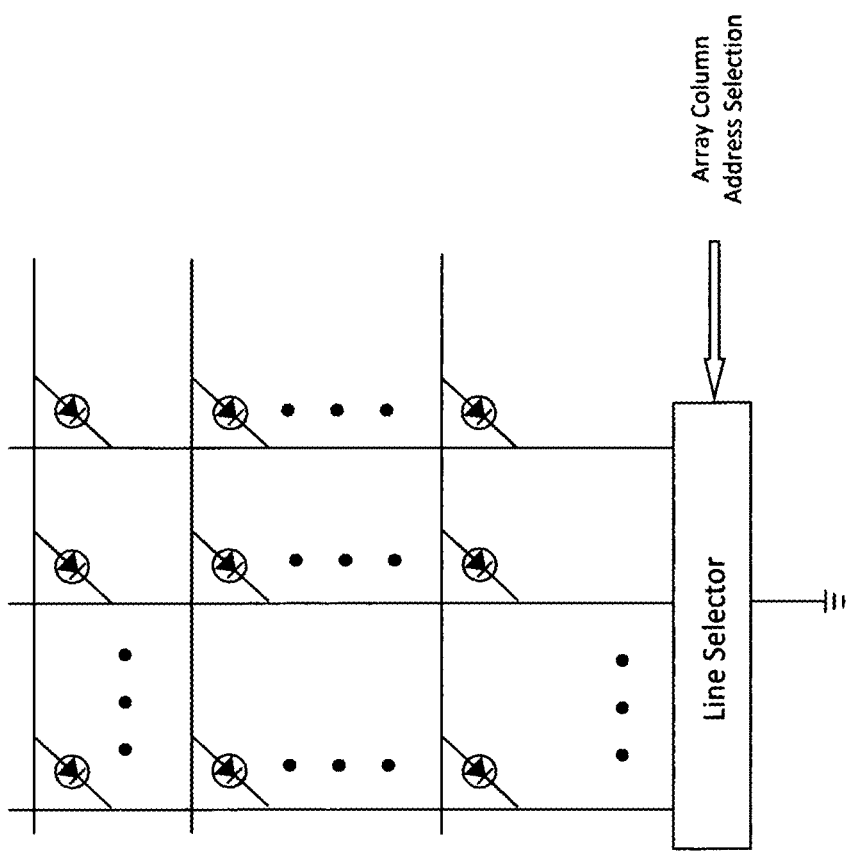
FIG. 6 depicts an adaptation of the arrangement depicted in FIG. 5 that is controlled by an address decoder so that the selected subset can be associated with a unique binary address.
Figure 7:
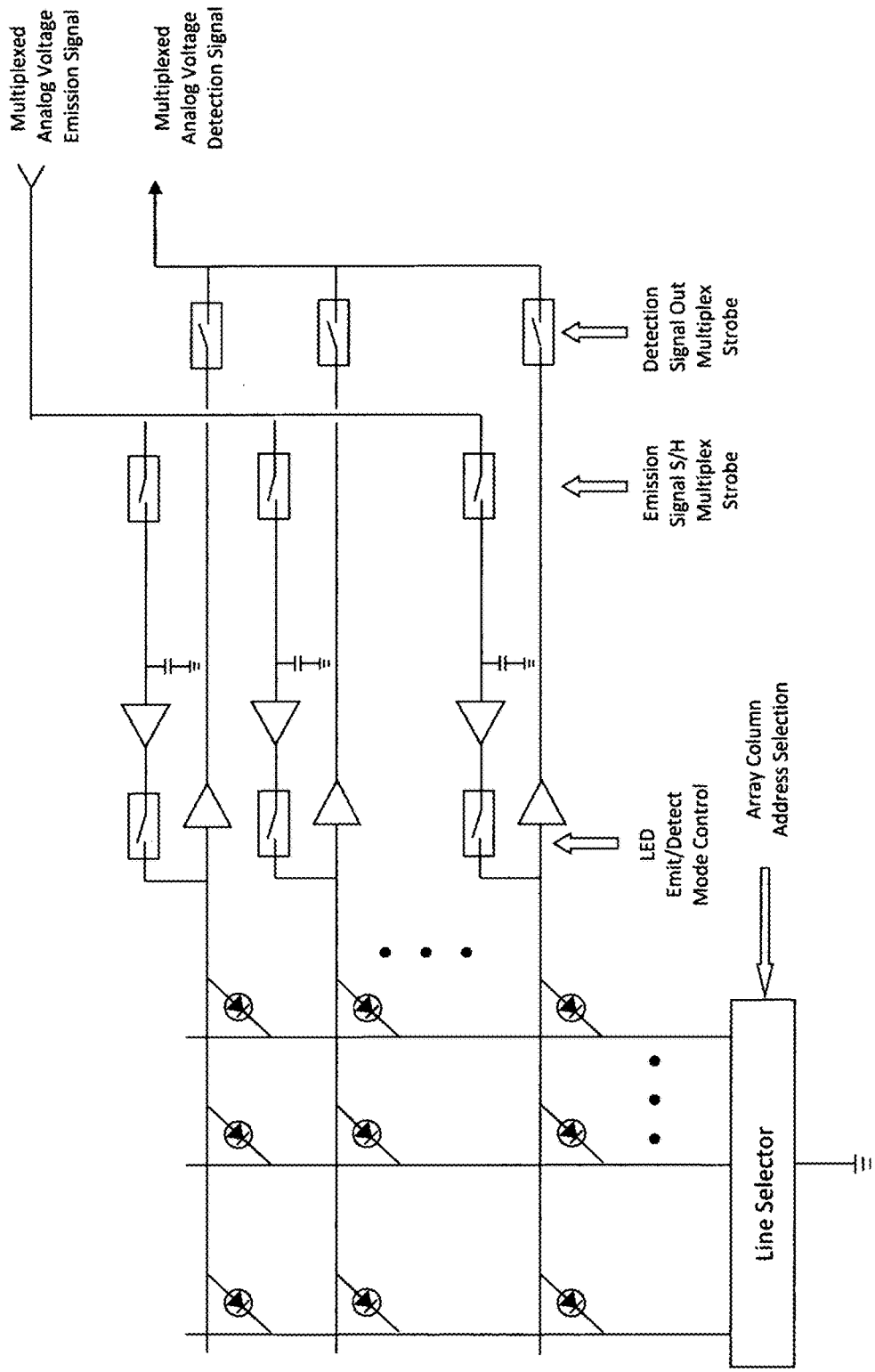
FIG. 7 depicts an example adaptation of the arrangement of FIG. 6 together to form a highly scalable LED array display that also functions as a light field detector.

FIG. 7 depicts an example adaptation of the arrangement of FIG. 6 together to form a highly scalable LED array display that also functions as a light field detector. The various multiplexing switches in this arrangement can be synchronized with the line selector and mode control signal so that each LED very briefly provides periodically updated detection measurement and is free to emit light the rest of the time. A wide range of variations and other possible implementations are possible and implemented in various embodiments of the present invention.

Figure 8:
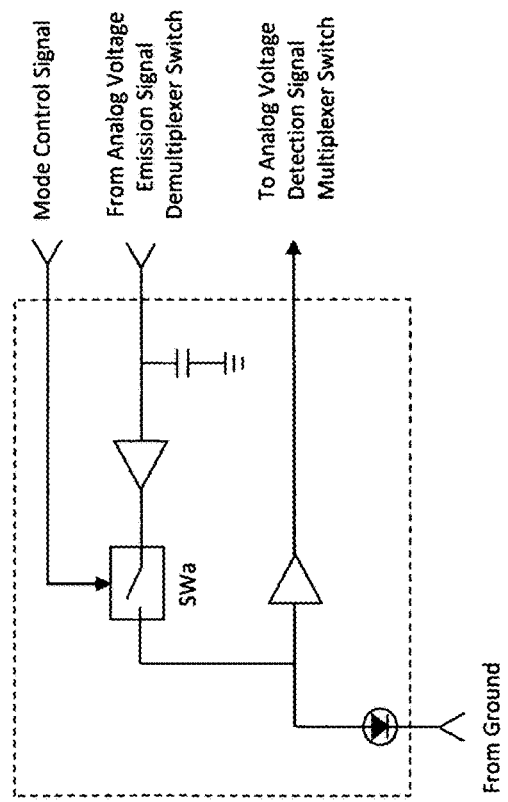
FIGS. 8 and 9 depict example functional cells that can be used in a large scale array.
Figure 9:
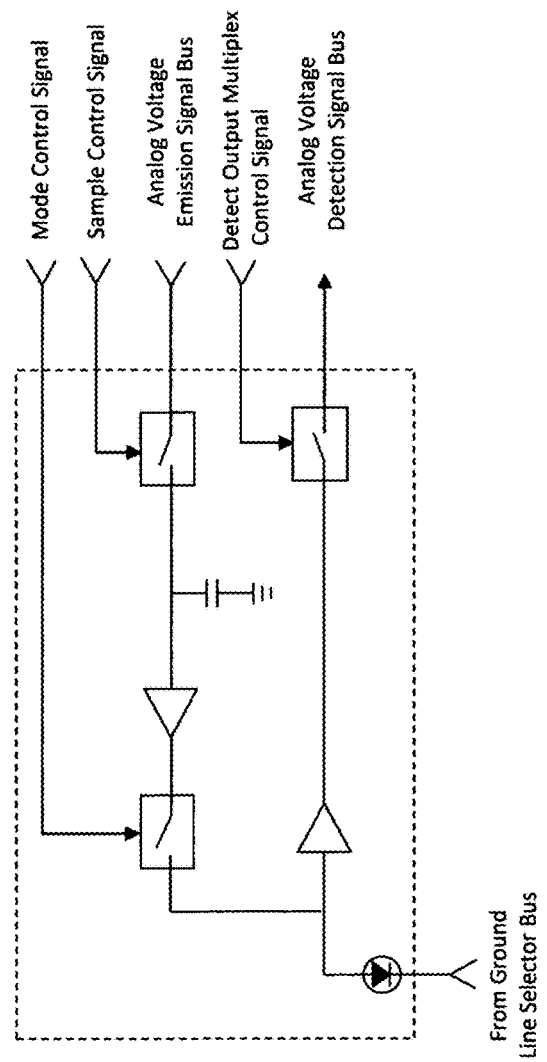

Such time-division multiplexed arrangements can alternatively be used for selectively measuring voltages or currents of each individual LED. Further, the illumination and measurement time-division multiplexed arrangements themselves can be time-division multiplexed, interleaved, or merged in various ways. As an illustrative example, the arrangement of FIG. 7 can be reorganized so that the LED, mode control switch, capacitor, and amplifiers are collocated, for example as in the illustrative example arrangement of FIG. 8. Such an arrangement can be implemented with, for example, three MOSFET switching transistor configurations, two MOSFET amplifying transistor configurations, a small-area/small-volume capacitor, and an LED element (that is, five transistors, a small capacitor, and an LED). This can be treated as a cell which is interconnected to multiplexing switches and control logic. A wide range of variations and other possible implementations are possible and the example of FIG. 7 is in no way limiting. For example, the arrangement of FIG. 7 can be reorganized to decentralize the multiplexing structures so that the LED, mode control switch, multiplexing and sample/hold switches, capacitor, and amplifiers are collocated, for example as in the illustrative example arrangement of FIG. 9. Such an arrangement can be implemented with, for example, three MOSFET switching transistor configurations, two MOSFET amplifying transistor configurations, a small-area/small-volume capacitor, and an LED element (that is, five transistors, a small capacitor, and an LED). This can be treated as a cell whose analog signals are directly interconnected to busses. Other arrangements are also possible.

The discussion and development thus far are based on the analog circuit measurement and display arrangement of FIG. 10 that in turn leverages the photovoltaic properties of LEDs. With minor modifications clear to one skilled in the art, the discussion and development thus far can be modified to operate based on the analog circuit measurement and display arrangements of FIG. 11 and FIG. 12 that leverage the photocurrrent properties of LEDs.

Figure 15:
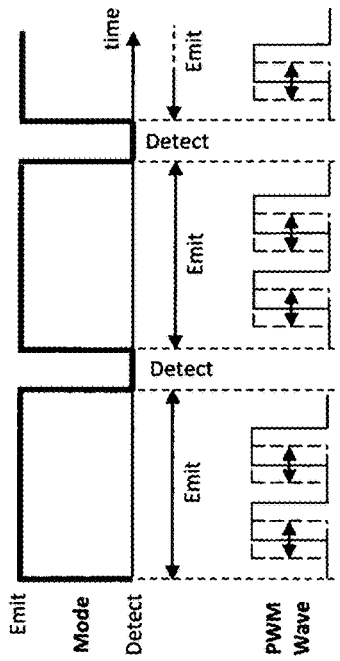
FIGS. 14-16 depict adaptations of the digital circuit measurement and display arrangements into an example combination.
Figure 16:
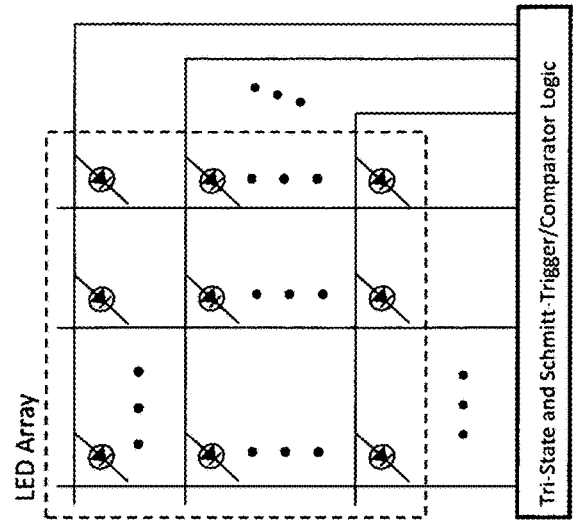
Figure 14:
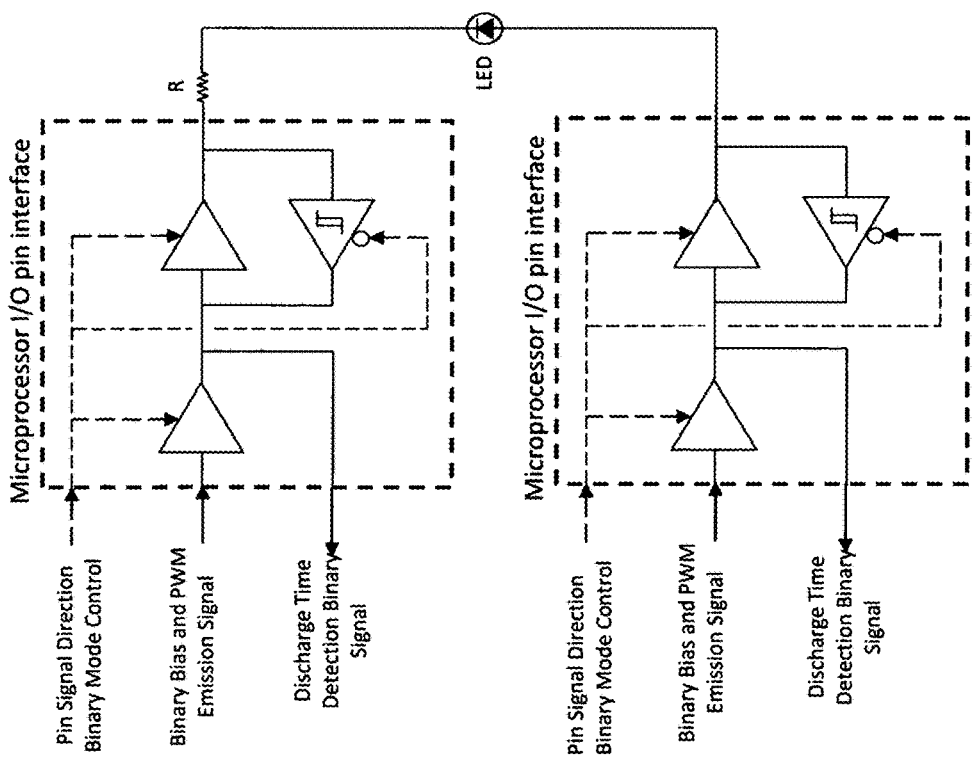

FIG. 14, FIG. 15, and FIG. 16 depict an example of how the digital circuit measurement and display arrangement of FIG. 13 (that in turn leverages discharge times for accumulations of photo-induced charge in the junction capacitance of the LED) can be adapted into the construction developed thus far. FIG. 14 adapts FIG. 13 to additional include provisions for illuminating the LED with a pulse-modulated emission signal. Noting that the detection process described earlier in conjunction with FIG. 13 can be confined to unperceivably short intervals of time, FIG. 15 illustrates how a pulse-width modulated binary signal can be generated during LED illumination intervals to vary LED emitted light brightness. FIG. 16 illustrates an adaptation of the tri-state and Schmitt-trigger/comparator logic akin to that illustrated in the microprocessor I/O pin interface that can be used to sequentially access subsets of LEDs in an LED array as described in conjunction with FIG. 5 and FIG. 6.

FIGS. 17-19 depict example state diagrams for the operation of the LED and the use of input signals and output signals described above. From the viewpoint of the binary mode control signal there are only two states: a detection state and an emission state, as suggested in FIG. 17. From the viewpoint of the role of the LED in a larger system incorporating a multiplexed circuit arrangement such as that of FIG. 7, there can be a detection state, an emission state, and an idle state (where there is no emission nor detection occurring), obeying state transition maps such as depicted in FIG. 18 or FIG. 19. At a further level of detail, there are additional considerations. To emit light, a binary mode control signal can be set to "emit" mode (causing the analog switch to be closed) and the emission light signal must be of sufficient value to cause the LED to emit light (for example, so that the voltage across the LED is above the "turn-on" voltage for that LED). If the binary mode control signal is in "emit" mode but the emission light signal is not of such sufficient value, the LED will not illuminate. This can be useful for brightness control (via pulse-width modulation), black-screen display, and other uses. In some embodiments, this can be used to coordinate the light emission of neighboring LEDs in an array while a particular LED in the array is in detection mode. If the emission light signal of such sufficient value but the binary mode control signal is in "detect" mode, the LED will not illuminate responsive to the emission light signal. This allows the emission light signal to be varied during a time interval when there is no light emitted, a property useful for multiplexing arrangements. During a time interval beginning with the change of state of the binary mode control signal to some settling-time period afterwards, the detection output and/or light emission level may momentarily not be accurate. To detect light, the binary mode control signal must be in "detect" mode (causing the analog switch to be open). The detected light signal can be used by a subsequent system or ignored. Intervals where the circuit is in detection mode but the detection signal is ignored can be useful for multiplexing arrangement, in providing guard-intervals for settling time, to coordinate with the light emission of neighboring LEDs in an array, etc.

FIG. 20 depicts an example state transition diagram reflecting the above considerations. The top "Emit Mode" box and bottom "Detect Mode" box reflect the states of an LED from the viewpoint of the binary mode control signal as suggested by FIG. 17. The two "Idle" states (one in each of the "Emit Mode" box and "Detect Mode" box) of FIG. 20 reflect (at least in part) the "Idle" state suggested in FIG. 18 and/or FIG. 19. Within the "Emit Mode" box, transitions between "Emit" and "Idle" can be controlled by emit signal multiplexing arrangements, algorithms for coordinating the light emission of an LED in an array while a neighboring LED in the array is in detection mode, etc. Within the "Detect Mode" box, transitions between "Detect" and "Idle" can be controlled by independent or coordinated multiplexing arrangements, algorithms for coordinating the light emission of an LED in an array while a neighboring LED in the array is in detection mode, etc. In making transitions between states in the boxes, the originating and termination states can be chosen in a manner advantageous for details of various multiplexing and feature embodiments. Transitions between the groups of states within the two boxes correspond to the vast impedance shift invoked by the switch opening and closing as driven by the binary mode control signal. In FIG. 20, the settling times between these two groups of states are gathered and regarded as a transitional state.

As mentioned earlier, the amplitude of light emitted by an LED can be modulated to lesser values by means of pulse-width modulation (PWM) of a binary waveform. For example, if the binary waveform oscillates between fully illuminated and non-illuminated values, the LED illumination amplitude will be perceived roughly as 50% of the full-on illumination level when the duty-cycle of the pulse is 50%, roughly as 75% of the full-on illumination level when the duty-cycle of the pulse is 75%, roughly as 10% of the full-on illumination level when the duty-cycle of the pulse is 10%, etc. Clearly the larger fraction of time the LED is illuminated (i.e., the larger the duty-cycle), the brighter the perceived light observed emitted from the LED.

It is further understood that depending on the embodiments of light sourcing and sensing arrangements of the present invention, various combinations and modifications of multiplexing circuitry can be implemented to achieve the desired result. It is further understood that such multiplexing circuitry can further be combined and modified to better utilize the properties of flexible materials onto which the light LEDs, OLEDs, etc. are printed.

1.3 Light Sourcing and Light Sensing Geometries

FIGS. 21a-21d shows example geometries of light emitting and light sensing arrangements for various optical tomography systems. Various light emitting and light sensing arrangement geometries suitable for optical tomography include, but are not limited to planar, cylindrical, spherical, or warped (i.e., flexible). For example, FIG. 21a shows an example light emitting and light sensing arrangement with planar geometry. FIG. 21b shows an example light emitting and light sensing arrangement with cylindrical geometry. FIG. 21c shows an example light emitting and light sensing arrangement with spherical geometry. FIG. 21d shows an example light emitting and light sensing arrangement with warped, or flexible geometry. In certain embodiments, one plane or one half of the arrangement can act as a light sensing array and the other plane or half can act as a light emitting or light emission array, or both planes or both halves can have both light emitting and light sensing capabilities. Depending on the physical characteristics of the object or specimen, the medium in which the object is located, size, opacity, etc., various geometric arrangements can be advantageous and can be implemented in different embodiments of the present invention. It is also noted that in certain embodiments of the invention, flexible, printable materials can be used to achieve a variety of geometric arrangements of the present invention.

1.3 Discretization of 3-D Space in Measurement Volume

FIG. 22 shows an example embodiment of a discretized space between a planar light emitting and light sensing arrangement in an optical tomography system. In order to calculate the transparency of an object placed between a light emitting and light sensing arrangement with high resolution, a set of mathematical equations for processing can be generated. To generate mathematical equations, space between the light emitting and light sensing arrangement is discretized, such as into a plurality of cubes, or voxels, as depicted in FIG. 22, which shows an example embodiment of a discretized space between a planar light emitting and light sensing arrangement in an optical tomography system. These cubes act as 3D pixels, or voxels, and are interrogated to generate a full reconstruction of the object. Just as a camera captures a 2D image by interrogating and replicating the color of each pixel in the image, the present invention renders a 3D model of an object by interrogating and replicating the opacity of each voxel in the object.

Figure 23B:
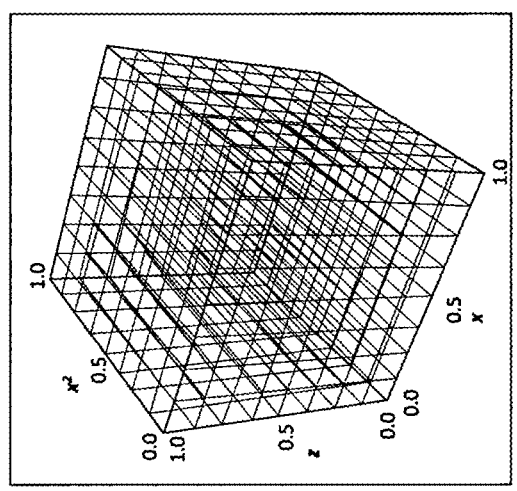
FIG. 23b shows an example of a discretized three-dimensional space between a planar light emitting and light sensing arrangement.
Figure 23A:
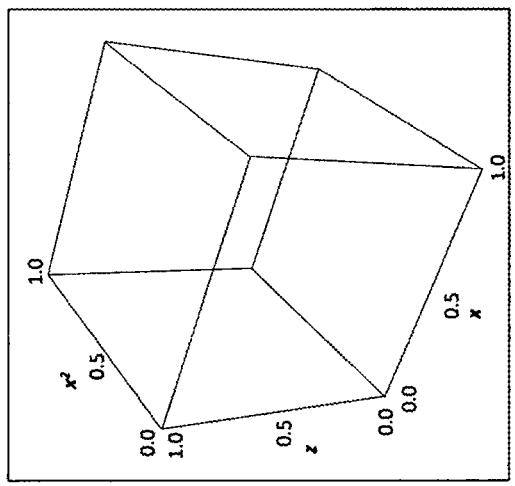
FIG. 23a shows an example of three-dimensional space between a planar light emitting and light sensing arrangement.

FIG. 23a shows an example of three-dimensional space between a planar light emitting and light sensing arrangement. FIG. 23b shows an example of a discretized three-dimensional space between a planar light emitting and light sensing arrangement. Generally, an increase in the discretization of the space into smaller units provides a more detailed calculation of the transparency of the object and hence, a higher resolution. The set of equations and associated computations will vary in complexity based on the geometry of the arrangement.

Figure 24C:
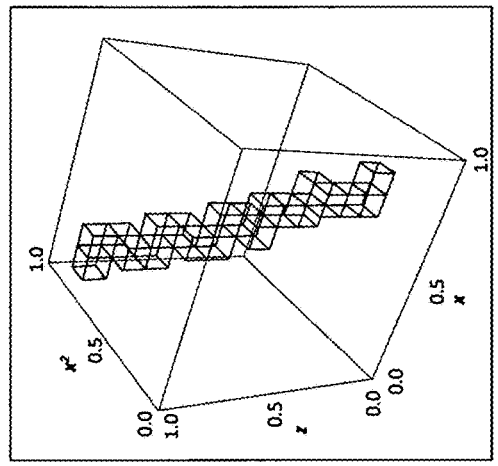
FIG. 24c further depicts an example activation of discrete voxels intersected by the light path in discretized three-dimensional space.
Figure 24B:
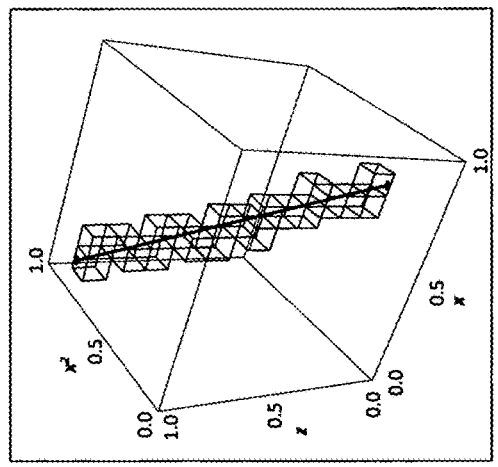
FIG. 24b depicts an example activation of discrete voxels intersected by the light path in discretized three-dimensional space.
Figure 24A:
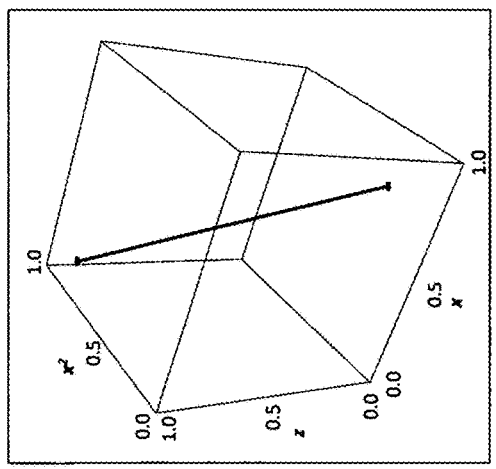
FIG. 24a depicts an example light path between a light emission plane and a light sensing plane in three-dimensional space.
Figure 25A:
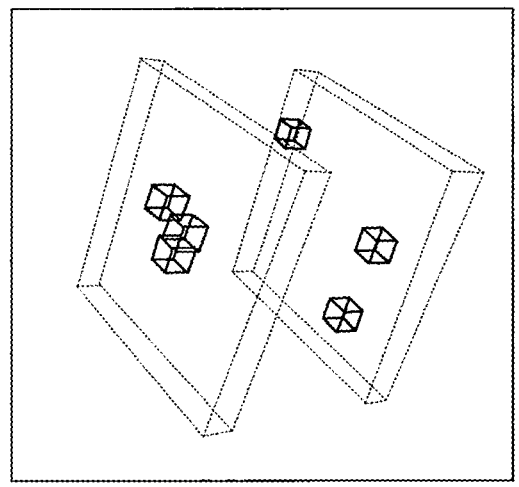
FIG. 25a depicts discretized planes in a discretized space, shown with voxels activated by multiple light paths.
Figure 25B:
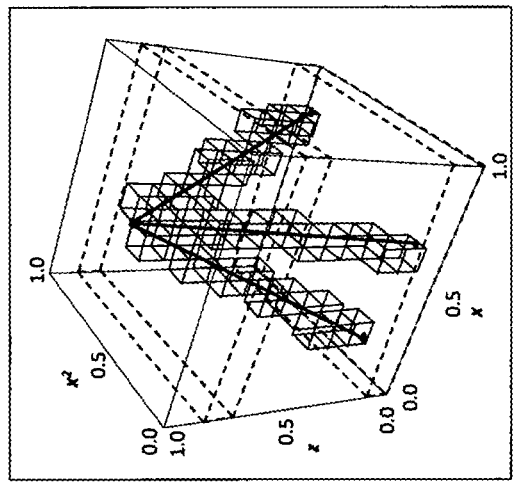
FIG. 25b depicts an example cross-sectional view of a voxel arrangement in a discretized space.

In an example embodiment, the space between the light emitting and light sensing arrangement is divided into voxels as in FIG. 23b. One LED on the light emitting array would transmit every possible light path (as a cone of light) through the discretized space between the emitting LED and each light sensing element on the light sensing array. For example, FIG. 24a depicts an example light path between a light emitting plane and a light sensing plane in three-dimensional space. FIG. 24b depicts an example activation of discrete voxels intersected by the light path in discretized three-dimensional space. FIG. 24c further depicts an example activation of discrete voxels intersected by the light path in discretized three-dimensional space. Additionally, FIG. 25a depicts discretized planes in a discretized space, shown with voxels activated by multiple light paths. FIG. 25b depicts an example cross-sectional view of a voxel arrangement in a discretized space. For each light path such as those shown in FIG. 25a, the present invention will calculate which voxels the light path intersects, calculate the length of the light path passing through each voxel, and calculate the opacity of each voxel that the light path intersects. In a planar arrangement, the light emitting and light sensing arrays have n by n or $n^2$ LEDs and there will be at most $n^4$ light paths because each light path is defined by a pairing of light emitting and light sensing LEDs and there are $n^2 \times n^2 = n^4$ possible pairings of light emitting to light sensing LEDs. Consequently, there are also $n^4$ number of equations. Further, the number of voxels will vary from a minimum of $n^2$ wherein the distance between light emitting and sensing arrays is at a minimum and a maximum of $n^4$, wherein the number of unknowns are equal to the number of equations.

It is important to keep in mind the fact that this model is a gross approximation and oversimplification. It assumes that a light path between a light-emitting and light-sensing LED is an infinitesimally small line when in reality each light path is actually a whole group of light arrays with cylindrical thickness. This adds a second-order complexity to the calculations which can be implemented in certain embodiments of the present application. But briefly, because each light path now has thickness, one must account for the fact that a light path may intersect several voxels in one place at a time. Therefore when calculating the intersection length of the light path through each voxel, there are more parameters to consider.

1.4 Light Absorption Processes

Calculating the transmittance of a light path passing through several voxels can be calculated using Beer's law, which states that the transmission factor (fraction of light transmitted) for a path of length l and attenuation constant, a, is given by $T=e^{-al}$. Each voxel has an associated a value and a specific l value for every intersecting path of light, whereas each path of light has an associated T value. That means, for any given light path, there is one associated T value but n number of a and l values for n number of intersected voxels. In an example embodiment of the present invention, there are $n^3$ voxels and at most $n^4$ light paths, which yields a system of equations with $n^3$ unknown a values and at most $n^4$ transmittance equations (derived from Beer's Law). If all the T and l values are known for each equation within the system of equations, the a values can be calculated for each voxel. Because the system of equations is overdetermined (there are more equations than unknown variables), the a values should be calculated preferably using a pseudo-inverse technique to minimize the error. The calculated a values define the opacity for each voxel. Once the opacity of each voxel for the three dimensional space is calculated, the opacity of each voxel for the object also becomes known, and this data allows for the reconstruction of a three dimensional visualization of the object.

Figures 26A, 26B:
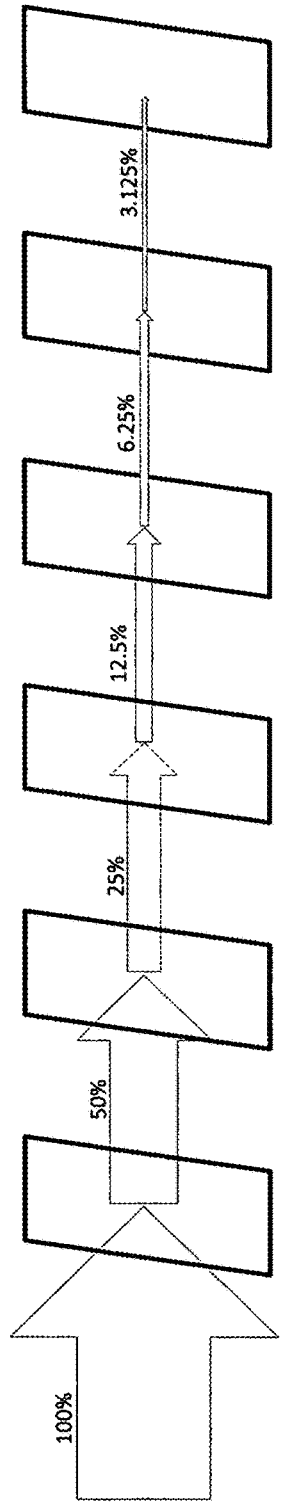
FIG. 26a depicts an example cascade of identical light transmission loss layers illustrating Beer's law.
FIG. 26b depicts an example set of data based on FIG. 26a showing a relationship between path length of light and light transmittance.

Some aspects of Beer's Law can further be illustrated by FIGS. 26a and 26b. FIG. 26a depicts an example cascade of identical light transmission loss layers illustrating Beer's law. As seen in Beer's law, the opacity of each voxel and the length of a light path traveling through that voxel affect the transmission loss of the light. For example, changing either the opacity factor or changing the length by a factor of 2 can decrease the fraction of light transmitted. FIG. 26b depicts an example set of data based on FIG. 26a showing a relationship between path length of light and light transmittance, wherein it is apparent that as the light path length increases, the transmittance of light decreases.

Beer's Law can also be described by FIGS. 27a and 27b. In contrast to FIG. 26a, FIG. 27a depicts an example cascade of non-uniform light loss transmission through objects of different thicknesses. FIG. 27b depicts an example set of data based on FIG. 27a showing a relationship between transmittance and percentage of light loss, wherein it is apparent that as the transmittance increases depending on the non-uniform thickness of objects, the percentage of correspondingly increases or decreases. Since Beer's Law is not a linear relationship but rather a relationship of exponential decay ($T=e^{-al}$), this means that depending on how many voxels are chosen to discretize a 3-D object or space, there will be different calculated T values. The more finely discretized the space, or in other words, the smaller the voxels are, the more voxels each light path must intersect to get from the light-emitting array to the light-sensing array.

The more voxels it intersects, the more the light gets attenuated, and the smaller the transmission value is.

2. First Model for Transmission-Based Tomography Computations

To better illustrate the above descriptions, this section explains a novel model of transmission-based tomography of 3-dimensional objects having at least partially transparent structures and surface boundaries (leveraging various associated conditions).

2.1 Indexing of Light Sensor Array and Light Emission Array

First assume a planar 2-dimensional light sensor array and a planar 2-dimensional light-emission array facing each other in a parallel arrangement configured so each sensor in the light sensor plane can receive light emitted by at least one light emitting element in the light emitting plane. Each light sensor element in the light sensor array has a unique index of the form $\{n_s, m_s\}$, where $n_s \in \{1,2, \ldots, N_s\}$ and $m_s \in \{1,2, \ldots, M_s\}$, and each light-emitting element has a unique index of the form $\{n_e, m_e\}$, where $n_e \in \{1,2, \ldots, N_e\}$ and $m_e \in \{1,2, \ldots, M_e\}$; accordingly the light sensor array comprises a total of $N_s M_s$ light-sensing elements and the light emitting array comprises a total of $N_e M_e$ light emitting elements.

2.2 Paths Between a Sensor in Light Sensor Array and Emitter in Light Emission Array Vs. Paths Between an Emitter in Light Emission Array and a Sensor in Light Sensor Array Each ordered quadruple, denoted by $$\{\{n_e, m_e\}, \{n_s, m_s\}\}$$

comprising a specific emitting light and sensing light in their respective arrays, defines a light path within the 3-dimensional discretized lattice. Think of the emitting light as the beginning of the light path and the sensing light as the destination of the light path. This path will be denoted by $$P(\{\{n_e, m_e\}, \{n_s, m_s\}\})$$

2.3 Intersection of Paths with Transparent Voxels

The 3-dimensional discretized lattice between the light emitting and light sensing arrays consists of a 3-dimensional array of voxels. In an example case, two n by n arrays of lights, one emitting and one sensing, facing each other at n distance apart will be discretized into $n^3$ adjacent individual cubes or voxels. These cubes are denoted by $C_{ijk}$, where ijk denotes a specific index for each cube with the following ranges:

$$\bigcup_{\substack{i \in [1,2,\ldots N] \\ j \in [1,2,\ldots N] \\ k \in [1,2,\ldots N]}} C_{ijk}$$

The light path determined by $\{\{n_e, m_e\}, \{n_s, m_s\}\}$ intersects a small subset of the $N^3$ cubes. A path that intersects cube $C_{ijk}$ travels through cube $C_{ijk}$ along a line segment inside the cube, and the length of this line segment (which typically varies from cube to cube along the path) can be denoted as $L_{ijk}$. As an example, FIG. 24c depicts an example activation of discrete voxels intersected by the light path in discretized three-dimensional space.

2.4 Total Transparency of a Path Intersecting Transparent Cubes

Again, a path that intersects cube $C_{ijk}$ travels through cube $C_{ijk}$ along a line segment inside the cube, and the length of this line segment (which typically varies from cube to cube along the light path) can be denoted as $L_{ijk}$.

There is a transmittance value for light, denoted as $T_{ijk}$, that is associated with each cube $C_{ijk}$ and the length of the light path $L_{ijk}$ through the cube $C_{ijk}$. Each cube has an associated attenuation constant $a_{ijk}$. In general this attenuation constant can vary with light wavelength, temperature, light polarization, and other factors. However for simplification dependency these factors will be omitted. As described above, according to Beer's law, the transmittance value T (fraction of light transmitted) for a path of length l and attenuation constant of value a is given by, $$T = e^{-al}$$

Thus for each cube $C_{ijk}$ intersected by the path $P(\{\{n_e, m_e\}, \{n_s, m_s\}\})$ with a path segment of length $L_{ijk}$, the transmittance value will be given by $$T_{ijk}(L_{ijk}) = e^{-a_{ijk} L_{ijk}}$$

Thus the transmittance value of the total path can be calculated as the product of the transmittance values of each cube $C_{ijk}$ in the path:

$$T(P(\{\{n_e, m_e\}, \{n_s, m_s\}\})) = \prod_{\{i,j,k\} \in P(\{\{n_e, m_e\}, \{n_s, m_s\}\})} T_{ijk}(L_{ijk})$$

$$= \prod_{\{i,j,k\} \in P(\{\{n_e, m_e\}, \{n_s, m_s\}\})} e^{-a_{ijk} L_{ijk}}$$

2.5 Aperture Effects of Individual Light Sensors and Light Emitters

An important additional consideration is the aperture effects of individual light sensors and light emitters. If uniform manufacturing with adequate tolerances can be assumed, additional mathematical models can be included (dependent, for example, on the angle of emitter or incident light paths). Alternately and advantageously, the system can be calibrated in a simpler approach. Amplitude measurements of the light can be made for each light path and stored with the sensing lights in the sensing array when there is no object placed between the light sensing and light emitting arrays. These measurements establish a "base case" scenario that can then be used to provide calibrating normalization factors for other non-base case scenarios. These path-by-path normalization factors associated with these aperture effects simply scale the measurement values used in the linear equations. For example, if a specific sensing light $\{n_s, m_s\}$ detects a light amplitude of $A_0$ for path $P(\{\{n_e, m_e\}, \{n_s, m_s\}\})$ without an object, and a light amplitude of $A_1$ with an object, then the normalized amplitude $A = A_1/A_0$.

Ideally the light emitter emits light for a path P with unit amplitude; for such an ideal case:

(measured received light amplitude) = (emitted light amplitude)·(transparency of path)

with
(emitted light amplitude)=1 and
(transparency of path)=T(P)
giving T(P)=(measured received light amplitude)

However, the emitted light amplitude can be expected to vary from path to path. Thus because of aperture effects it is more accurate to formulate the emitted light amplitude as a function of the path P, that is $A_{emit}(P)$. This gives $T(P) \cdot A_{emit}(P)$=(measured received light amplitude)

Similar path-dependent aperture effects can typically occur at the sensor as well. This can again be denoted with $A_{sense}(P)$. Including this consideration gives $T(P) \cdot A_{emit}(P) \cdot A_{sense}(P)$=(measured received light amplitude)

One can consolidate the two path-dependent aperture attenuations into a single function A(P), that is $A(P) = A_{emit}(P) \cdot A_{sense}(P)$.

Figure 28B:
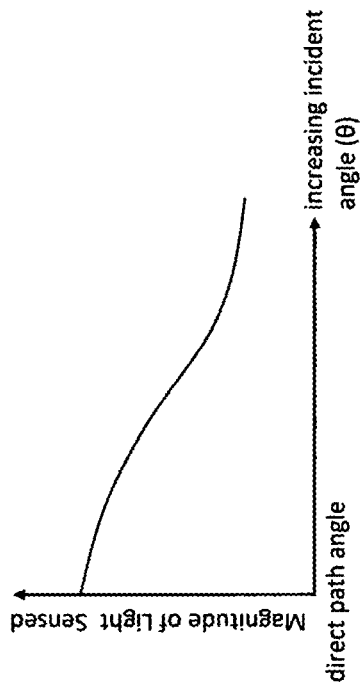
FIG. 28b depicts an example graph showing the relationship between magnitude of light sensed by a light sensing arrangement and the incident angle of the light path.
Figure 28A:
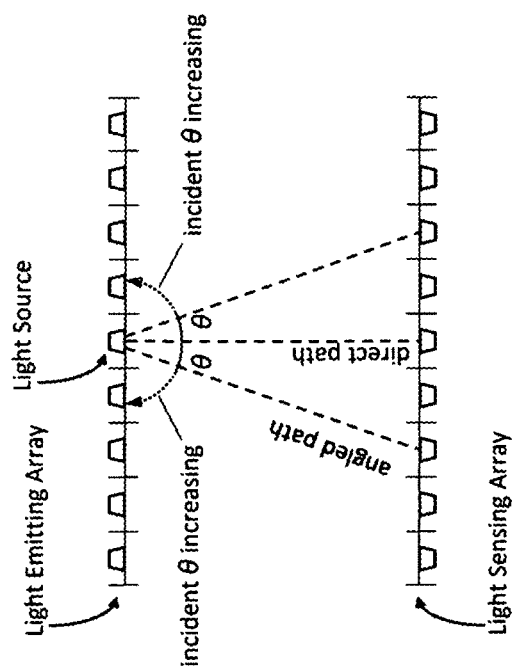
FIG. 28a depicts example aperture effects between a light emitting and light sensing arrangement in an optical tomography system.

Such a function A(P) can be measured empirically for a given specific implementation. Once known one can then write (for values of A(P)>0) the relation $T(P)$=(measured received light amplitude)/$A(P)$ FIG. 28a depicts example aperture effects between a light emitting and light sensing arrangement in an optical tomography system. FIG. 28b depicts an example graph showing the relationship between magnitude of light sensed by a light sensing arrangement and the incident angle of the light path. In reference to both FIGS. 28a and 28b, aperture effects can be described by the phenomenon that as the incident angle increases creating an angled path of light as opposed to a direct path of light, the amount of light sensed decreases.

Figure 29:
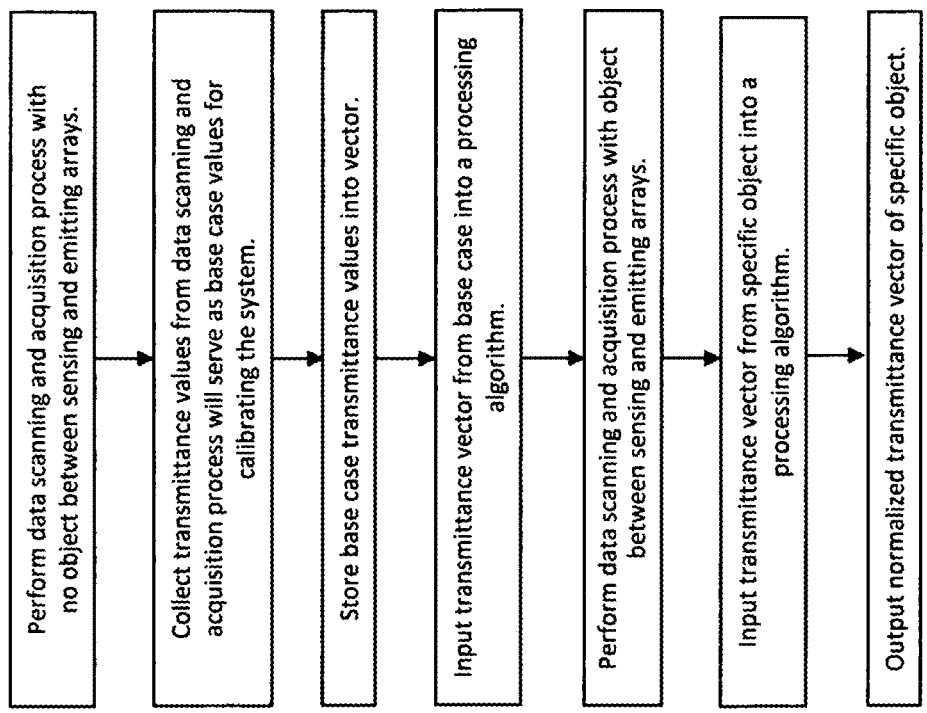
FIG. 29 depicts an example empirical aperture measurement and normalization flow chart to account for aperture effects that may occur between light emitting and light sensing arrangement in discretized three-dimensional space.

FIG. 29 depicts an example empirical aperture measurement and normalization flow chart to account for aperture effects that may occur between light emitting and light sensing arrangement in discretized three-dimensional space. In other terms, FIG. 29 illustrates an example process of how the system is calibrated to account for aperture effects. An algorithm designed to normalize data takes in two inputs, a transmittance vector of a base case scenario when no object is present between sensing and emitting arrays and, a transmittance vector of a specific scenario when a specific object is being imaged. The algorithm uses the base case scenario to normalize the transmittance vector of the specific scenario for more accurate measurements and calculations. A variety of software programming languages and environments can be used to implement the steps described in the flow chart and can be later adapted for scattering effects.

2.6 Use of Logarithms to Transform Total Transparency of a Path into a Linear Equation Taking the log of the above equation results in $\log(\text{measurement}(P)/A(P)) = \log(T(P))$ giving $\log(\text{measurement}(P)) - \log(A(P)) = \log(T(P)) = \Sigma \log(T_{ijk}(L_{ijk}))$ $\{i,j,k\} \in P(\{\{n_e,m_e\}\{n_s,m_s\}\})$ $\Sigma \log(e^{-a_{ijk}L_{ijk}})$ $\{i,j,k\} \in P(\{\{n_e,m_e\}\{n_s,m_s\}\}) = -\Sigma a_{ijk}L_{ijk}$ $\{i,j,k\} \in P(\{\{n_e,m_e\}\{n_s,m_s\}\})$

2.7 Use of Multiple Paths to Build a System of Linear Equations

Groups of equations such as constructed above $\log(\text{measurement}(P)) - \log(A(P)) = -\Sigma a_{ijk}L_{ijk}$ $\{i,j,k\} \in P(\{\{n_e,m_e\}\{n_s,m_s\}\})$ can be used to create a system of equations. That is, a selected group of paths together form a collection P* of paths $P^* = \{P(\{\{n_e,m_e\},\{n_s,m_s\}\})\}$.

For each path $P \in P^*$ (each P is $P_{(\{\{n_e,m_e\},\{v_s,m_s\}\})}$), a transmittance value T(P) can be measured, and the collection of lengths $\{L_{ijk}\}$ for each cube intersected by the light path can be calculated with geometry.

2.8 Adequate Number of Equations

The individual attenuation constants $\{a_{ijk}\}$ associated with each cube, or voxel $\{C_{ijk}\}$, can then be treated as unknown variables, which can then be solved for if the collection of paths P* consist of enough linearly-independent equations.

2.9 Over-Specified System of Equations

Figure 30B:
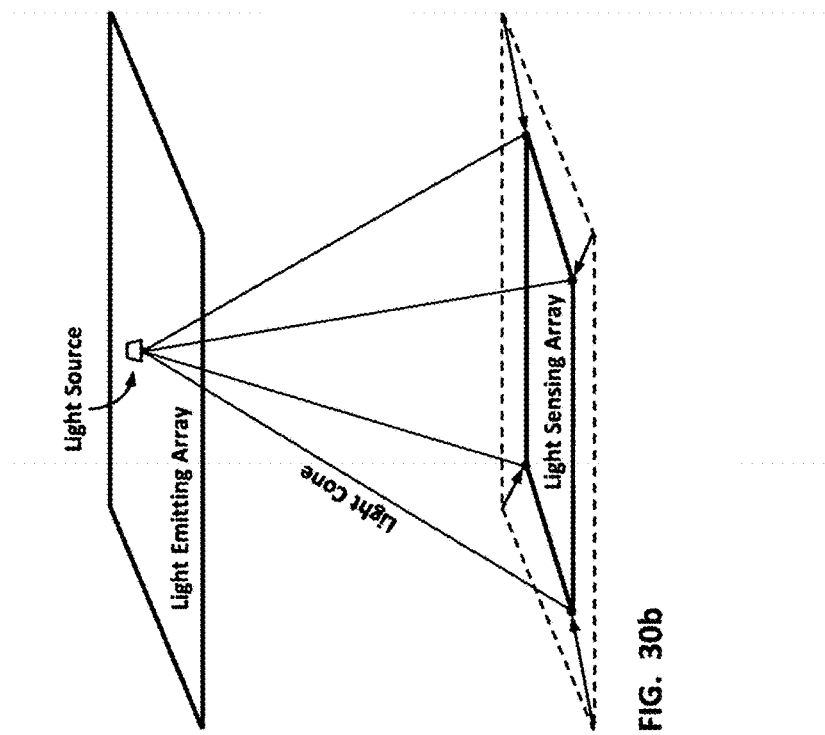
FIG. 30b depicts an example planar geometry light emitting and light sensing arrangement wherein the emitting and sensing planes are of different dimensions.
Figure 30A:
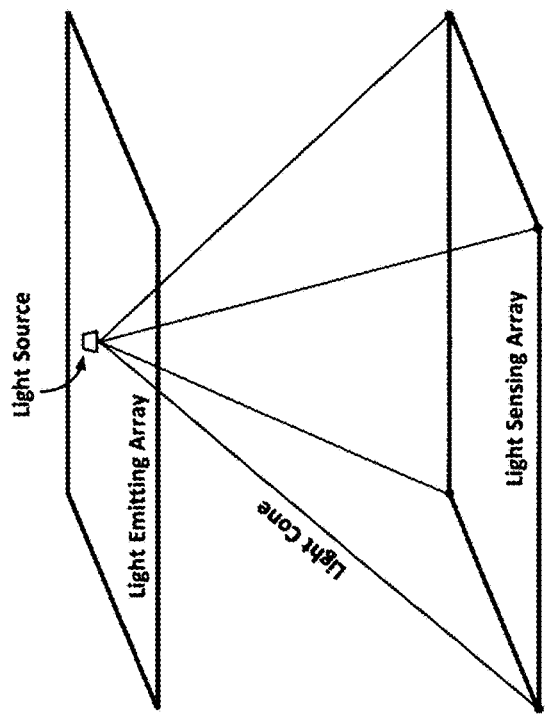
FIG. 30a depicts an example planar geometry light emitting and light sensing arrangement wherein the emitting and sensing planes are of the same dimensions.
Figure 31:
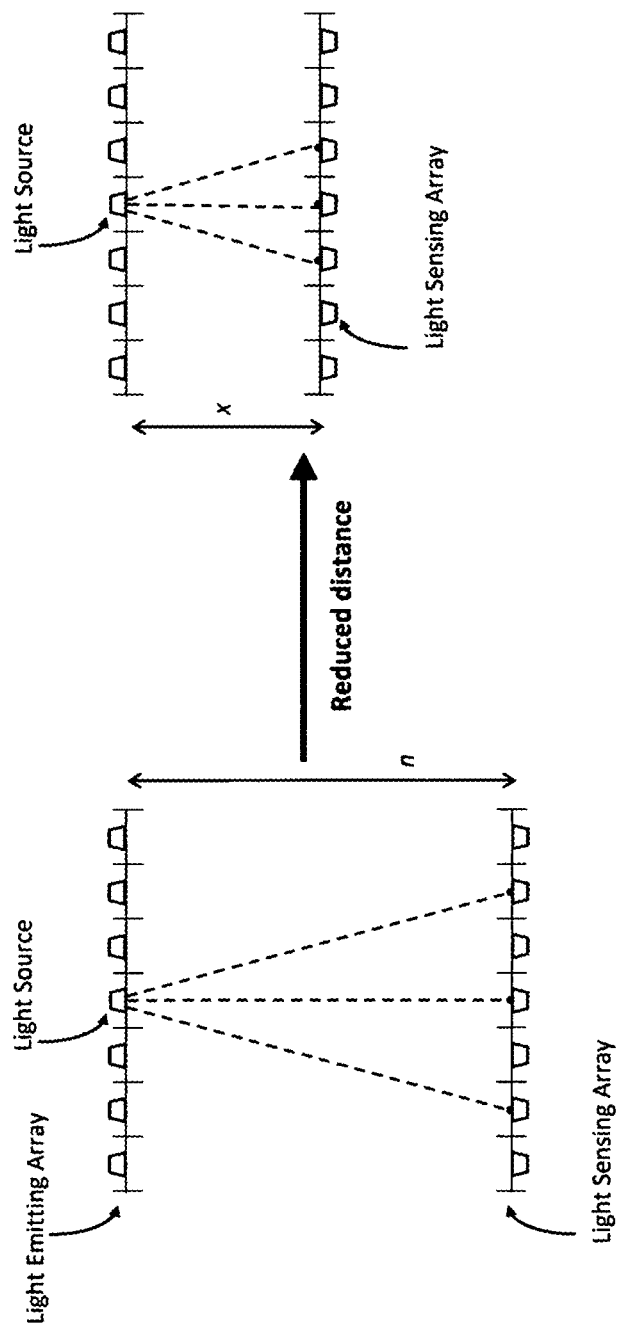
FIG. 31 depicts an example planar geometry light emitting and sensing arrangement wherein the distance between emitting and sensing planes is reduced.

If the measurements can be expected to be noisy or non-ideal, it can be advantageous for the collections of paths P* to have more equations than unknown variables so as to create an over-specified system of (potentially inconsistent) linear equations. The over-specified system can be solved with a generalized inverse operation such as the Moore-Penrose Generalized Inverse, which finds the solution that minimizes the error. In certain embodiments, however, it can be advantageous to reduce computational processing and increase efficiency, which can be achieved through reducing the number of equations. FIG. 30a depicts an example planar geometry light emitting and light sensing arrangement wherein the emitting and sensing planes are of the same dimensions. FIG. 30b depicts an example planar geometry light emitting and light sensing arrangement wherein the emitting and sensing planes are of different dimensions. In having differing dimensions of the emitting and sensing planes, fewer equations are generated and therefore, computations are reduced. Another way to reduce computational processing is based on FIG. 31. FIG. 31 depicts an example planar geometry light emitting and light sensing arrangement wherein the distance between emitting and sensing planes is reduced, thereby reducing the number of light paths and overall computational processing.

2. Example Sizings and Coordination of Indexing

The mathematics is simpler if $n_e = n_s$ and $m_e = m_s$ and if the light sensor plane and light emitter planes are consistent and aligned so that the sensor element indices, emitter element indices, and cube indices are subsets of a common indexed lattice. However, the invention provides for a wide range of variations, array sizes, configurations, and other choices for the light sensor arrays and a wide range of different variations, array sizes, configurations, and other choices for the light emission arrays.

3. Example Physical Implementation

Now we will illustrate in greater detail the software and hardware implementation of the invention including an example of the data path associated with the invention.

3.1 Example Software Implementation

Figure 32:
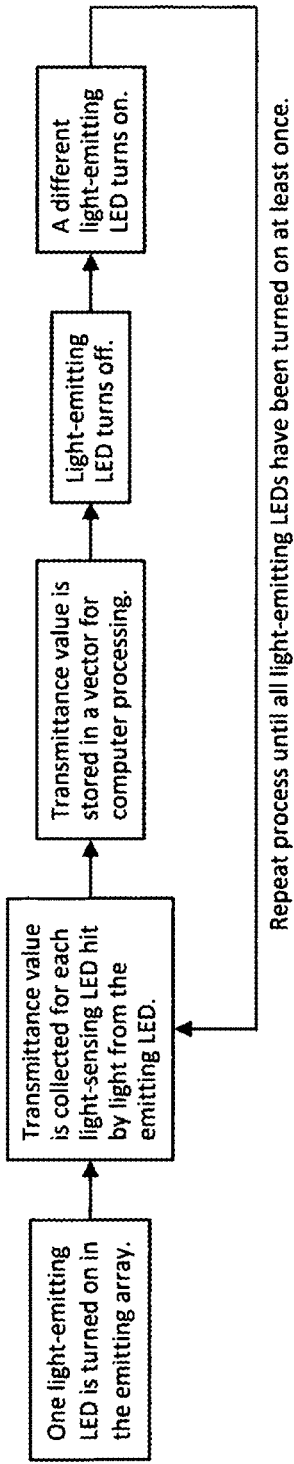
FIG. 32 depicts an example measurement data scanning and acquisition flow chart for data gathered by the light sensing array about an object placed between light emitting and light sensing arrangement in discretized three-dimensional space.

FIG. 32 depicts an exemplary measurement data scanning and acquisition flow chart for data gathered by the light sensing array about an object placed between light emitting and light sensing arrangement in discretized three-dimensional space. A first light-emitting LED is turned on in the emitting array. Then, a transmittance value is collected for each light-sensing LED that senses light from the emitting LED. The transmittance value is then stored in a vector for computer processing. The first light-emitting LED then turns off and a different light-emitting LED turns on. This process repeats until all light-emitting LEDs have been turned on at least once. In one embodiment, a computer processing system can be used to provide coordinates to control the measurement data scanning and acquisition, including controlling of the LEDs turning on or off. FIG. 32 is example and is not limited by the order shown in the flow chart. A variety of software programming languages and environments can be used to implement the steps described in the flow chart.

Figure 33:
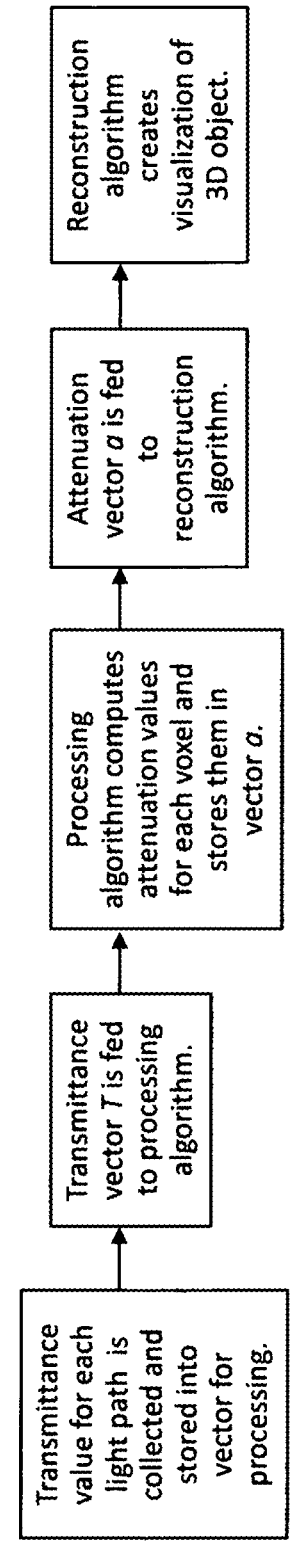
FIG. 33 depicts an example measurement data processing flow chart for data gathered by the light sensing array about an object placed between light emitting and light sensing arrangement in discretized three-dimensional space.

FIG. 33 depicts an example measurement data processing flow chart for data gathered by the light sensing array about an object placed between light emitting and light sensing arrangement in discretized three-dimensional space. In this example, a transmittance value for each light path is collected and stored into a vector T for processing. This vector T is fed to a processing algorithm (i.e., using Matlab™), which computes attenuation values for each voxel and stores them in a vector a. Attenuation vector a is then fed to a 3D reconstruction algorithm (i.e., using MathematicaTm), which creates a visualization of the 3D object. FIG. 33 is example and is not limited by the order shown in the flow chart. A variety of software programming languages and environments can be used to implement the steps described in the flow chart.

3.2 Example Hardware Implementation and Data Path

Figure 34:
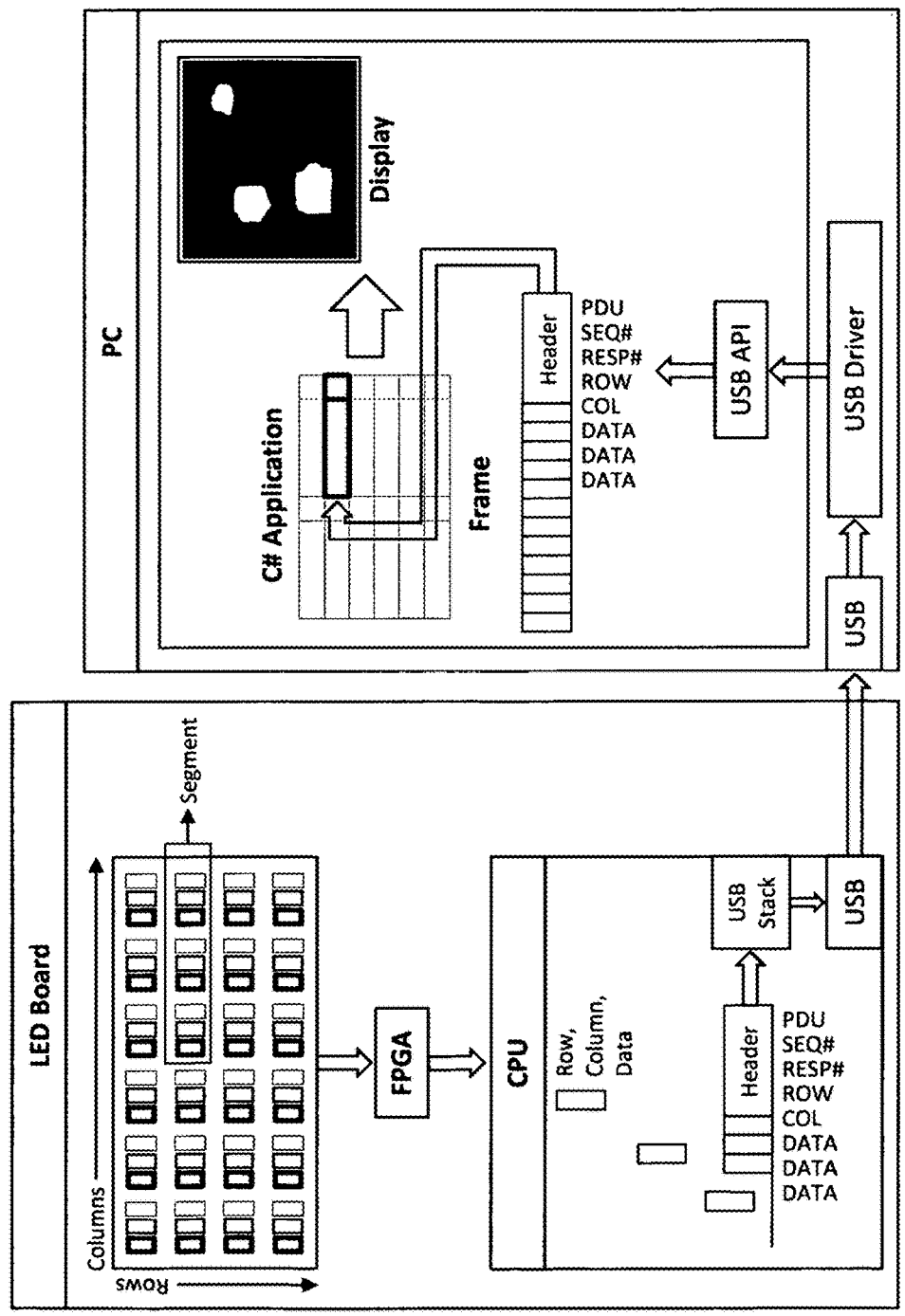
FIG. 34 depicts an example hardware and software architecture implementation in an optical tomography system for a data path.

FIG. 34 depicts an example hardware and software architecture implementation in an optical tomography system for a data path. Data path generally refers to how data is processed from hardware to the software associated with the invention. Referring to FIG. 34, the hardware would typically include but is not limited to the LED sensor array, a field programmable gate array, an embedded processor, a USB stack, USB link, a computer—with a USB driver, USB, API, software for controlling the invention, memory, data storage, a display, etc. The embedded CPU communicates with the FPGA and retrieves from the FPGA the information for each individual sensor. The embedded CPU uses its RAM to assemble all the individual sensor data into a frame. The concept of a frame provides the benefit of "synchronizing" the data elements into the concept of one sensor image or frame, defined by a unique time stamp. That concept can then have additional attributes such as capture settings, sequence number, etc. Technically it is also a natural concept in the USB and Ethernet interfaces, with a natural 1-to-1 mapping. Each frame is then sent by the embedded CPU to the computer via USB or Ethernet. Typically, UDP packets would be a good choice to stream the frames efficiently over a reliable network. If reliability is an issue, TCP can be implemented and a "frame start pattern" can be added to sync/resync to the start of each frame within the byte-oriented TCP stream. The computer software application, can be written in a programming language such as C#/.NET, using a standard Microsoft™ USB driver for the HID device class. Configuring the embedded CPU USB stack to present itself as a HID device has the advantage of being very universally compatible with any operating system and its native drivers. The software application makes calls to the driver layer at regular intervals in order to retrieve any data that may have accumulated in the internal queue of the driver. Then, the application performs some transformations in order to generate the graphical data and display it. This includes linear mapping to color range, application of linear calibration correction, etc.

Figure 35:
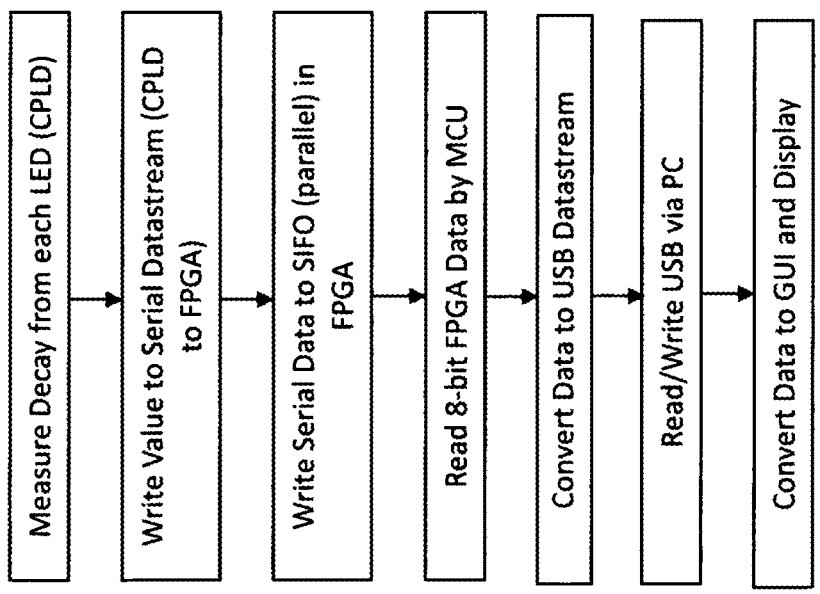
FIG. 35 depicts an example method illustrating steps in the flow of the data path of the invention.

FIG. 35 depicts an example method illustrating steps in the flow of the data path of the invention.

Alternative embodiments using a variety of computing hardware and software can be implemented depending on the amount of data, required performance, etc.

4. Effects of Refraction, Reflection, and Light Scattering

The present application can also be configured to account in various degrees for various aspects of the effects of refraction, reflection, and light scattering.

FIG. 36a depicts an example of refraction of a light path transmitted through a transparent object between light emitting and light sensing arrangement.

FIG. 36b depicts an example of light scattering of a light path transmitted through a translucent object between light emitting and light sensing arrangement.

Figure 36C:
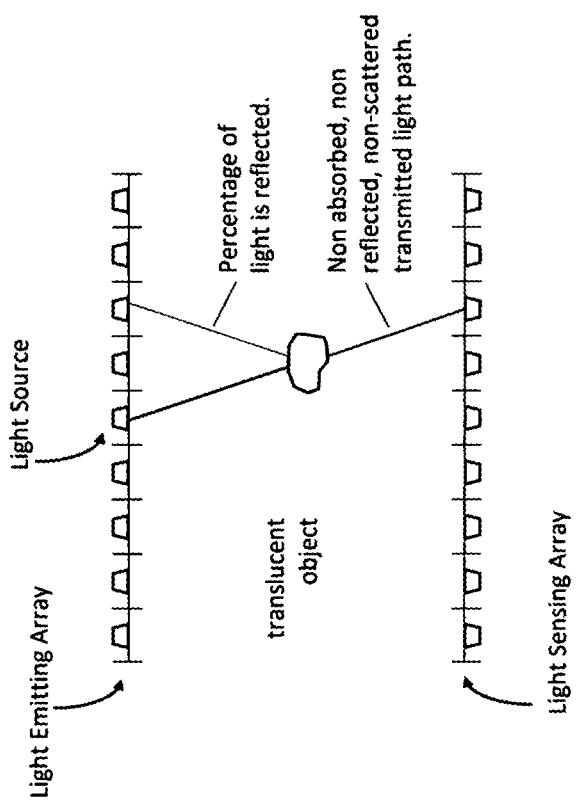
FIG. 36c depicts an example of reflection of a light path through a transparent object between light emitting and light sensing arrangement.

FIG. 36c depicts an example of reflection of a light path through a transparent object between light emitting and light sensing arrangement.

5. Cylindrical Geometry Arrangements

5.1 Cylindrical Light Emitting and Sensing Arrangement

Figure 37C:
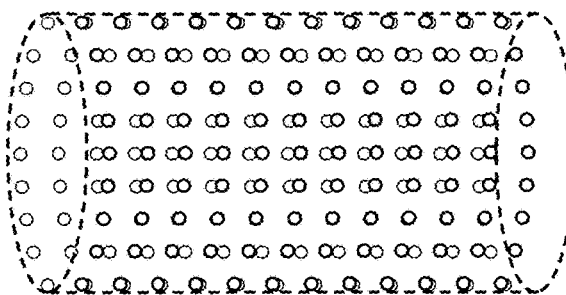
FIG. 37c depicts the LED arrangement of FIG. 37b with an arrangement of LEDs on a front side and back side of the cylindrically shaped system.
Figure 37B:
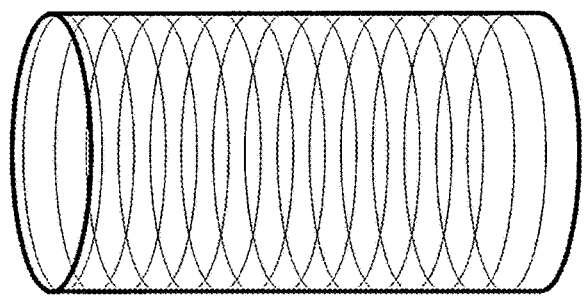
FIG. 37b depicts the arrangement of FIG. 37a with a row-like arrangement of LEDs in a cylindrically shaped system.
Figure 37A:
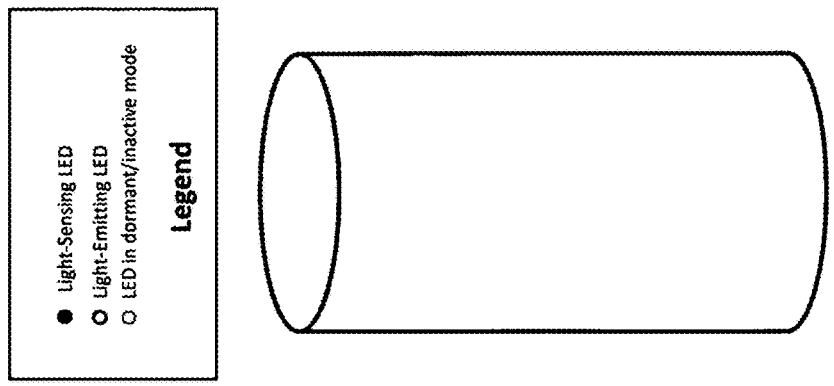
FIG. 37a depicts an example light emitting and light sensing arrangement with cylindrical geometry in an optical tomography system.
Figure 37F:
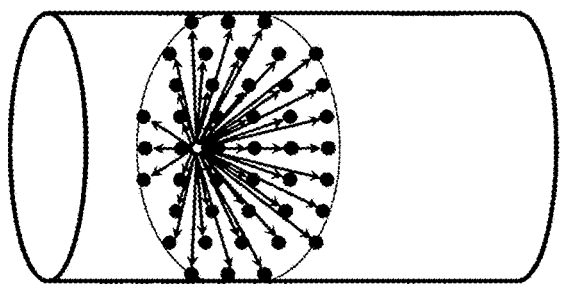
FIG. 37f depicts an example emitting LED emitting light from the back side of the cylindrically shaped system to the front side wherein a plurality of sensing LEDs sense the emitted light.
Figure 37E:
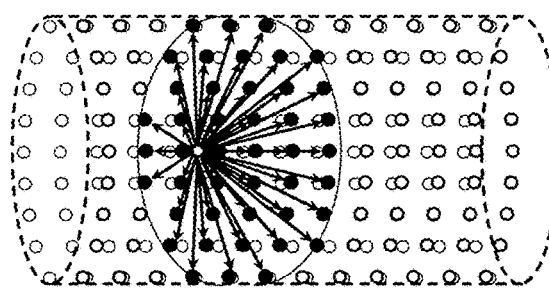
FIG. 37e depicts an example emitting LED emitting light in and among LEDs in an emitting array from the back side of the cylindrically shaped system to the front side wherein a plurality of sensing LEDs sense the emitted light among LEDs in a sensing array.
Figure 37D:
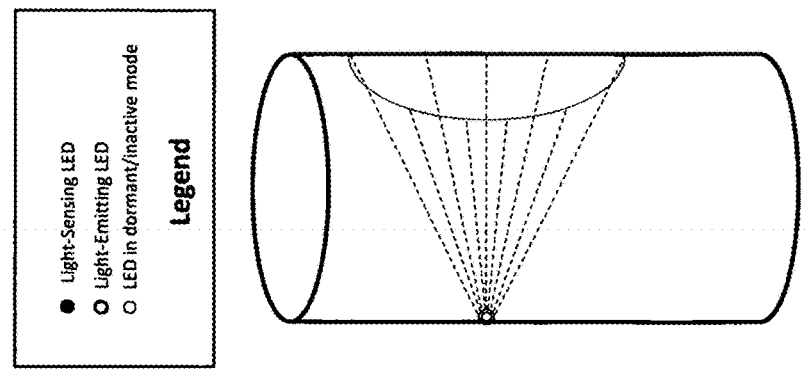
FIG. 37d depicts an example side view of emitting LED from the back side of the cylindrically shaped system to the front side.

As mentioned previously, various embodiments of the invention can include a variety of geometric arrangements. One example of alternate geometric arrangements of value are those that are cylindrical. FIG. 37a depicts an example light emitting and light sensing arrangement with cylindrical geometry in an optical tomography system. FIG. 37b depicts the arrangement of FIG. 37a with a row-like arrangement of LEDs in a cylindrically shaped system. FIG. 37c depicts the LED arrangement of FIG. 37b with an arrangement of LEDs on a front side and back side of the cylindrically shaped system. FIG. 37d depicts an example side view of emitting LED from the back side of the cylindrically shaped system to the front side. FIG. 37e depicts an example emitting LED emitting light in and among LEDs in an emitting array from the back side of the cylindrically shaped system to the front side wherein a plurality of sensing LEDs sense the emitted light among LEDs in a sensing array. FIG. 37f depicts an example emitting LED emitting light from the back side of the cylindrically shaped system to the front side wherein a plurality of sensing LEDs sense the emitted light.

Figure 37H:
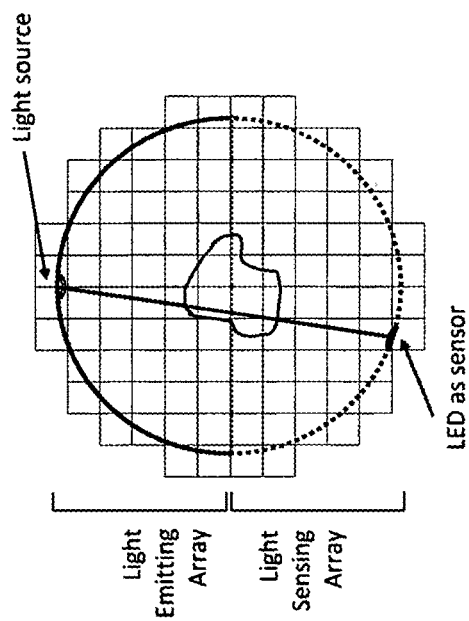
FIG. 37h depicts a top view of an example discretization of a light emitting and light sensing arrangement with cylindrical geometry in an optical tomography system.
Figure 37G:
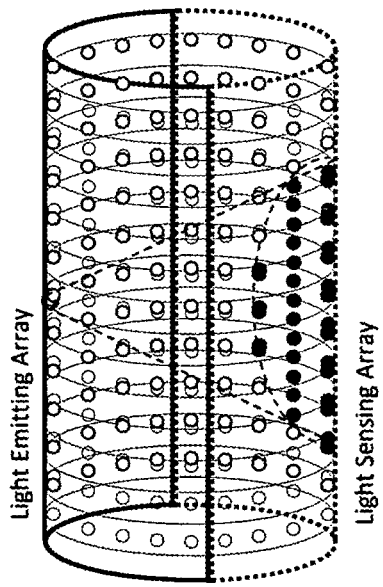
FIG. 37g depicts a more detailed and rotated view of the cylindrical arrangement of FIG. 37a, showing an emitting array and a sensing array.

A cylindrical arrangement can have a variety of embodiments. An example embodiment is FIG. 37g, which depicts a more detailed and rotated view of the cylindrical arrangement of FIG. 37a, showing an emitting array and a sensing array. Each of the two arrays form curved planes based on the curvature of the shape of the cylindrical structure implemented and shows an axis about which the cylinder is formed, for illustration purposes. FIG. 37g further shows a row-like arrangement of LEDs in more detail than FIG. 37b.

As with the planar light sensing and light emitting arrangement described earlier, the cylindrical arrangement can also be discretized into cubes, or voxels, but without perfect alignment with the curvature of the cylindrical structure. FIG. 37h depicts a top view of an example discretization of a light emitting and light sensing arrangement with cylindrical geometry in an optical tomography system. In FIG. 37h, it can be seen that the voxels lying both inside and outside the cylindrical structure, do not have precise alignment with the curvature of the cylindrical structure since the voxels lying both inside and outside the cylindrical arrangement do not perfectly align with the curvature of the cylindrical structure, the resulting attenuation constants for these voxels lying inside and outside the cylindrical arrangement will be an approximation, and will provide less accurate visualization of the object when the object is closer to the edge of the cylinder, as opposed to the object being placed towards the center of the cylindrical arrangement. Another approach that can be applied is to prorate the volume of the voxels that lie at the edge of the cylinder. This would provide an approximation with greater accuracy. Specifically, based on Beer's law, there is less accuracy because the $l_{ijk}$ values for the voxels lying inside and outside the cylindrical boundary of the cylindrical arrangement will be typically be an approximation since the length of light path passing through these voxels is only passing through part of the voxel. The effect of such approximations can be accounted for by various methods such as prorating the lengths light paths.

However, for many applications a cylindrical arrangement can be advantageous as opposed to a planar arrangement, due to the curvature of the cylindrical arrangement, providing a more detailed view of the object, since the LEDs are arranged at an angle, providing a greater number of direct light paths through the object. In other words, due to the curvature of the cylindrical arrangement, the number of direct light paths traveling through the object is optimized and since a direct path light has the greatest brightness, this increases the accuracy of the measurements taken by the system.

Further, in a cylindrical arrangement, LEDs can be co-optimized for both emitting and sensing properties in order to provide a 360 scan of the object, distinguishing it further from the planar arrangement described above.

While the planar arrangement view can be advantageous for planar objects such as a sample that has be sliced or flattened so as to be accommodated on a microscope slide, a cylindrical arrangement might provide for better resolution for spherical objects such as a sample examined without slicing or flattening.

The mathematical computations involved with a cylindrical arrangement are very similar to those of a planar arrange and still use Beer's Law. Again, Beer's Law defines the relationship between the transmittance of light with the length of a light path through an object and that object's opacity. Because of the different geometry, however, this law must be applied to different parameters. In the cylindrical case, we define three parameters: c, n, and A. The variable c represents the number of LEDs in a single row of LEDs in the cylindrical arrangement, n represents the number of rows of LEDs in the cylindrical arrangement, and A represents the number of voxels per row of LEDs (these as depicted in FIG. 37g), Therefore, in a cylindrical case, the number of voxels is equal to A*n and the maximum number of equations is given by $(n*(c/2))^2$ because there are $n*(c/2)$ light-emitting LEDs and $n*(c/2)$ light sensing LEDs. $n*(c/2)*n*(c/2)$ become the total possible number of pairings between each light-emitting and light-sensing LED; each pair defines a light path.

To apply Beer's Law, similar to the planar case, one must calculate the intersection path length of light for each light path. To do this, one must first define the position of each light-emitting LED and light-sensing LED in space. In a planar geometry, this is simpler because the z coordinates for the light-emitting and light-sensing planes are constant, so it is only necessary to calculate the x and y coordinates. In a cylindrical geometry, the z coordinates are no longer constant for each LED array because they are curved. Therefore, it is necessary to calculate the x, y, and z coordinates dependently. Such a calculation often can be simpler when using polar coordinates and then convert polar to Cartesian coordinates. Once the coordinates for each light-emitting and light-sensing LED is defined, it becomes very simple to calculate which voxels each light path intersects and the length of light that intersects each voxel, and it is exactly the same as the planar case.

Figure 38:
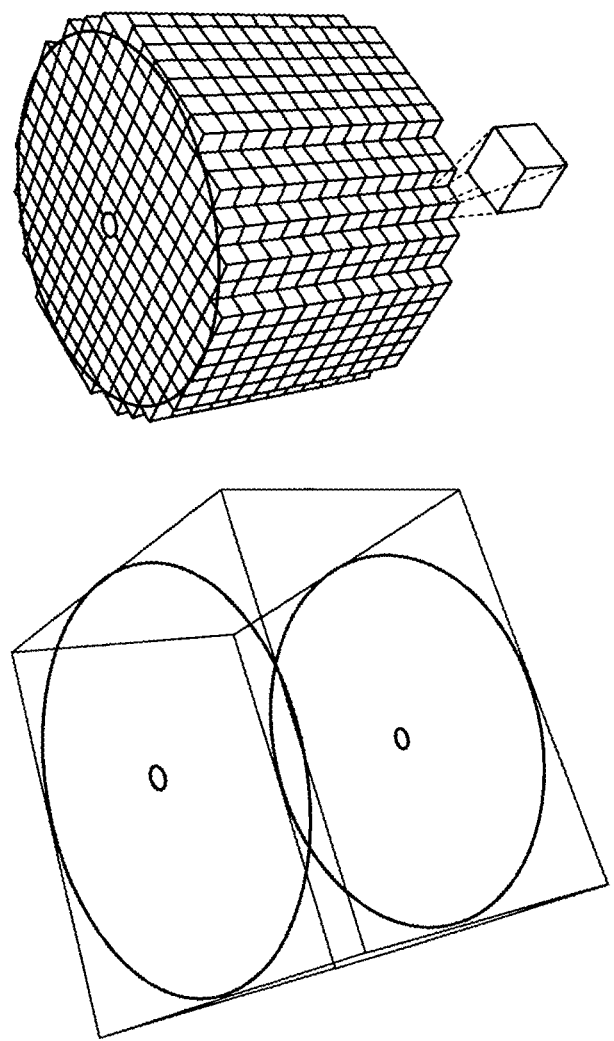
FIG. 38 shows an example embodiment of a discretization of space in a cylindrical light emitting and light sensing arrangement in an optical tomography system.
Figure 39B:
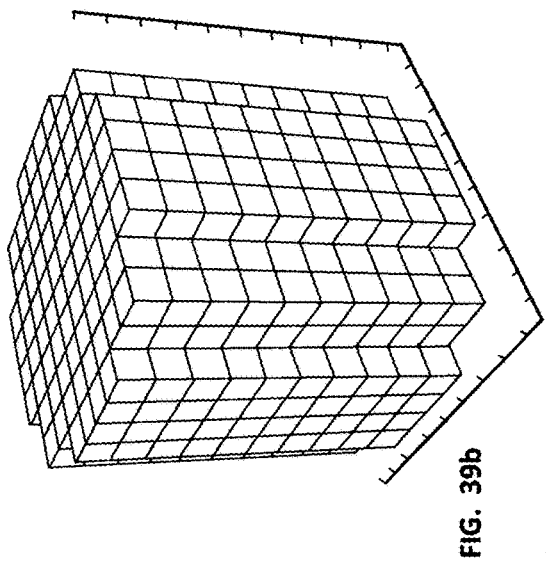
FIGS. 39a-39c show multiple views of an example embodiment of a discretization of space for a cylindrical light emitting and light sensing arrangement in an optical tomography system.
Figure 39A:
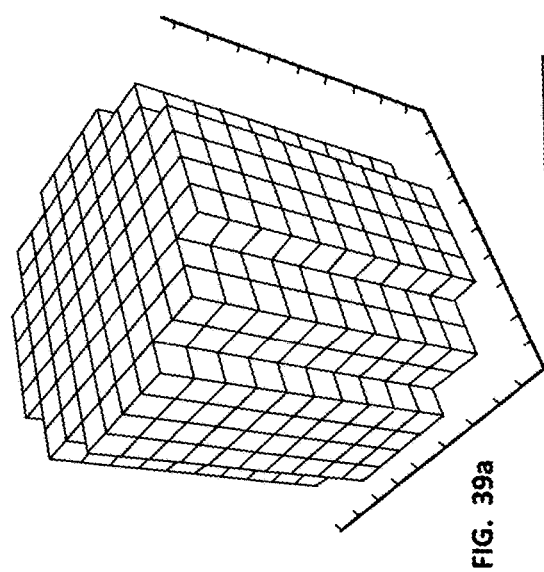
Figure 39C:
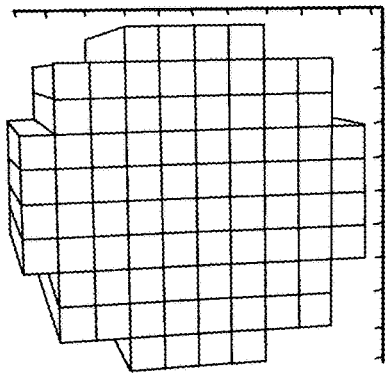
Figure 40B:
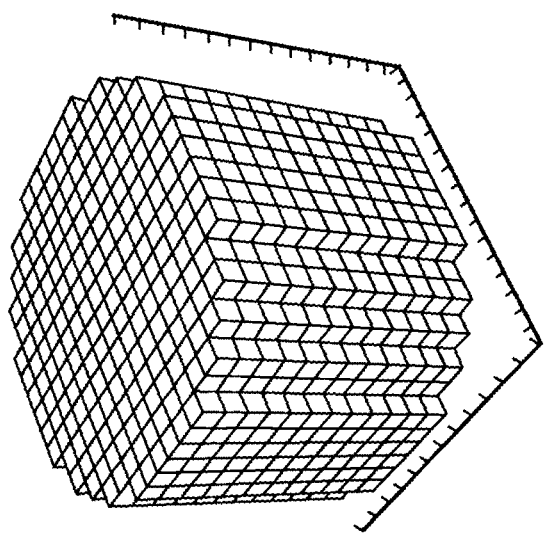
Figure 40A:
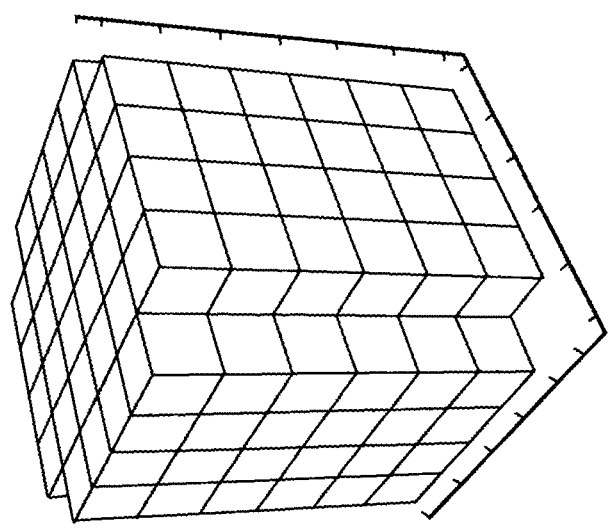
Figure 41B:
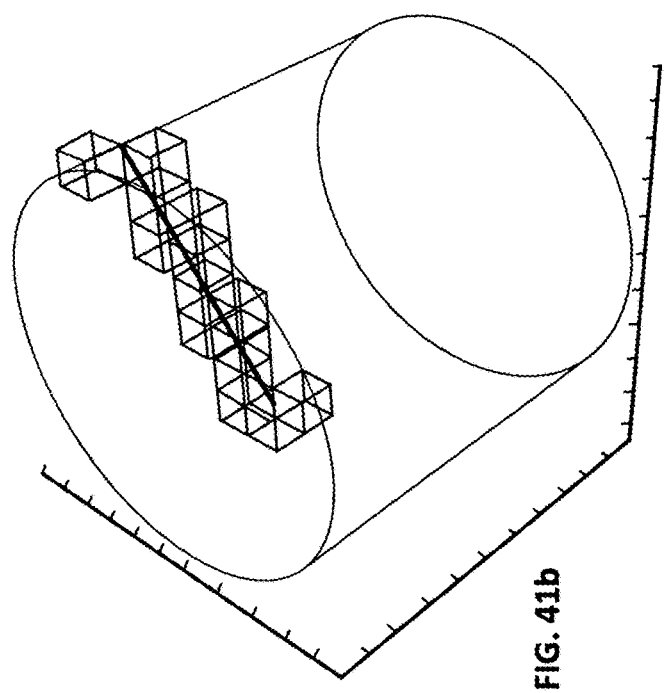
FIGS. 41a-41b depict an example activation of discrete voxels intersected by a light path in discretized three-dimensional space in a cylindrical arrangement in an optical tomography system.
Figure 41A:
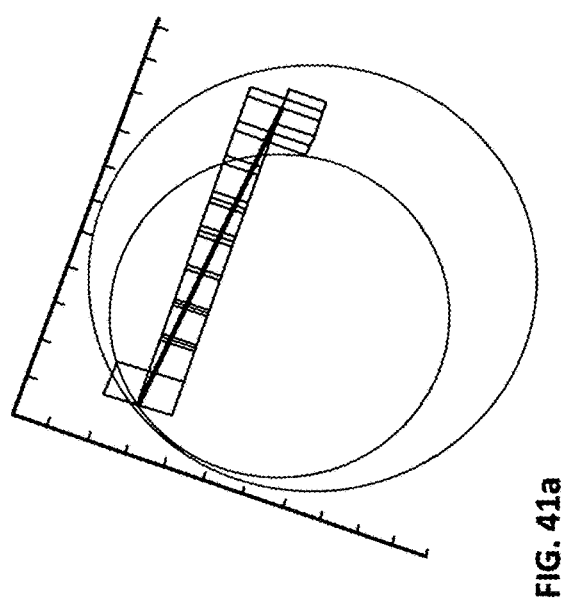

To better illustrate discretization of a cylindrical arrangement, FIG. 38 shows an example embodiment of a discretization of space in a cylindrical light emitting and light sensing arrangement in an optical tomography system. Further, FIGS. 39a-39c show multiple views of an example embodiment of a discretization of space for a cylindrical light emitting and light sensing arrangement in an optical tomography system. The amount of discretization can vary depending on the object being imaged, accuracy of approximation desired, etc. FIGS. 40a-40b show an example embodiment of a discretization of space for a cylindrical light emitting and light sensing arrangement in an optical tomography system, wherein FIG. 40b shows increased discretization. As shown in the planar arrangement above, FIGS. 41a-41b depict an example activation of discrete voxels intersected by a light path in discretized three-dimensional space in a cylindrical arrangement in an optical tomography system. Although the principle behind discretization remains generally the same whether the arrangement is planar or cylindrical, the computations and approximations associated with a specific measurement using a particular geometric arrangement can vary as illustrated above.

6. Example Holding Arrangements and Modules

The present invention can comprise a holding module for a variety of implementations and applications.

FIG. 42a illustrates an example sample holding module, as a slide with a well for a planar light emitting and light sensing arrangement in an optical tomography system for cytometry. In one embodiment, the holding module in FIG. 42a, is a well embedded into a transparent removable module with leg-type acting as supports for the removable module, which extend outside the boundaries of the LED arrays. In other embodiments, the holding module in FIG. 42a, as well the support structure can have different dimensions.

FIG. 42b illustrates a side view of the example holding module of FIG. 42a.

FIG. 43a illustrates an example holding module, as a pathway for a planar light emitting and light sensing arrangement in an optical tomography system. FIG. 43b illustrates a side view of the example holding module of FIG. 43a. The portions of pathway that extend past the 2 arrays can be parallel with the arrays, or can also be angled, as shown in FIG. 43b, to prevent compromise of samples (spilling, etc.) from gravity or other factors. The configuration in FIG. 43a can be useful in flow cytometry and microfluidic applications.

Figure 44A:
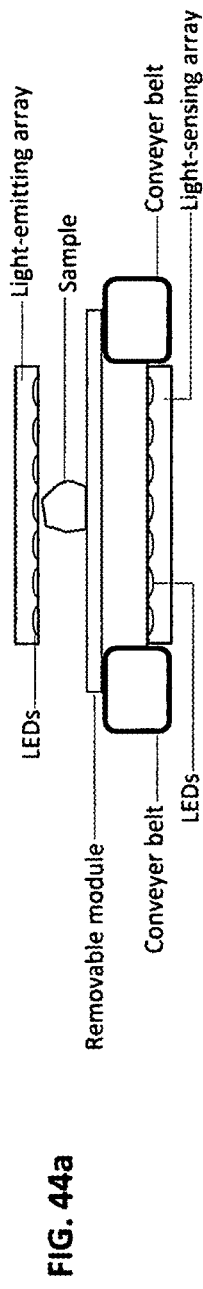
FIG. 44a illustrates an example holding module, as a belt configuration for a planar light emitting and light sensing arrangement in an optical tomography system.
Figure 44B:
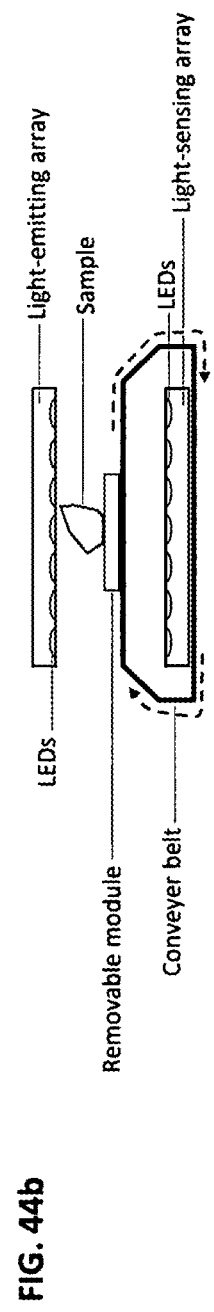

FIG. 44a illustrates an example holding module, as a belt configuration for a planar light emitting and light sensing arrangement in an optical tomography system. In FIG. 44a, a belt configuration, as seen front the front or back, with two conveyer belts, a transparent removable module that travels through the light-emitting and light-sensing arrays by way of 2 or more conveyor belts, which can extend outside the boundaries of the LED arrays to prevent corrupting a scan of the object. The sample can be deposited onto the module by way of a well, a pathway, or simply placed onto the module, in a way similar to a microscope slide.

Figure 45B:
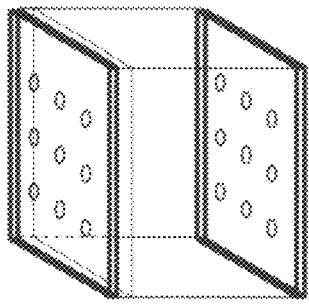
FIG. 45b illustrates another example holding module, as a shell configuration for a planar light emitting and light sensing arrangement in an optical tomography system.
Figure 45C:
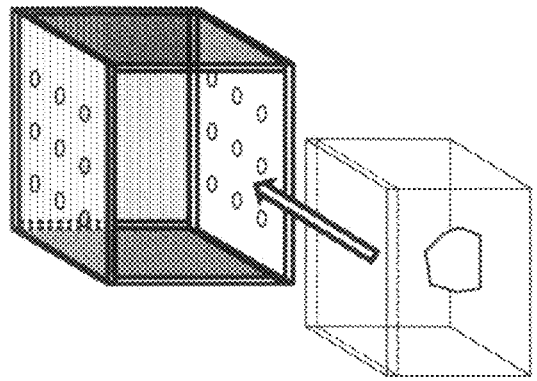
FIG. 45c illustrates yet another example holding module, as a shell configuration for a planar light emitting and light sensing arrangement in an optical tomography system.
Figure 45A:
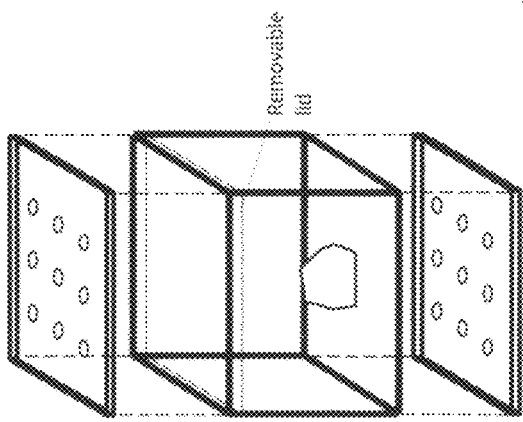
FIG. 45a illustrates an example holding module, as a shell configuration for a planar light emitting and light sensing arrangement in an optical tomography system.

FIG. 45a illustrates an example holding module, as a shell configuration for a planar light emitting and light sensing arrangement in an optical tomography system. The shell configuration illustrated in FIG. 45a a transparent removable module in the form of a transparent enclosure, which can have a variety of shapes depending on the harnessing of the module to the light emitting and sensing arrangement. One embodiment of this configuration is a cube with a removable lid, into which a sample can be inserted.

FIG. 45b illustrates another example holding module comprising a shell configuration for a planar light emitting and light sensing arrangement in an optical tomography system. The shell configuration illustrated in FIG. 45b comprises a transparent removable module in the form of a transparent enclosure, which can then be inserted between the arrays for scanning, in a stackable arrangement, as demonstrated by this figure which can have a variety of shapes depending on the harnessing of the module to the light emitting and sensing arrangement.

FIG. 45c illustrates yet another example holding module comprising a shell configuration for a planar light emitting and light sensing arrangement in an optical tomography system. In the configuration in FIG. 45c, the removable module holding a sample can be of a variety of sizes, and can be inserted into the configuration.

Figure 46C:
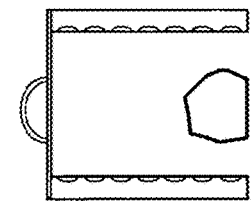
FIG. 46c illustrates the example holding module of FIG. 46a, wherein the handle is placed at a different location.
Figure 46B:
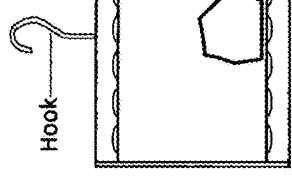
FIG. 46b illustrates an example holding module, as a hook configuration for a planar light emitting and light sensing arrangement in an optical tomography system.
Figure 46A:
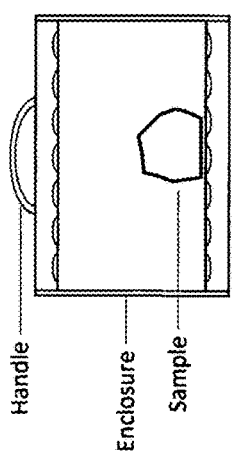
FIG. 46a illustrates an example holding module, as a handle configuration for a planar light emitting and light sensing arrangement in an optical tomography system.

FIG. 46a illustrates an example holding module comprising a handle configuration for a planar light emitting and light sensing arrangement in an optical tomography system. In the configuration of FIG. 46a, the removable module holding a sample can be of any size, and can be inserted into the configuration. Such an arrangement can be applied to a variety of configurations, to increase ease-of-use outside the traditional environment of a lab.

FIG. 46b illustrates an example holding module comprising a hook configuration for a planar light emitting and light sensing arrangement in an optical tomography system.

FIG. 46c illustrates the example holding module of FIG. 46a, wherein the handle is placed at a different location. Many other types of handle arrangements are anticipated and provided for by the invention, including wand, paddle, and various "dustpan"-like configurations.

Figure 46E:
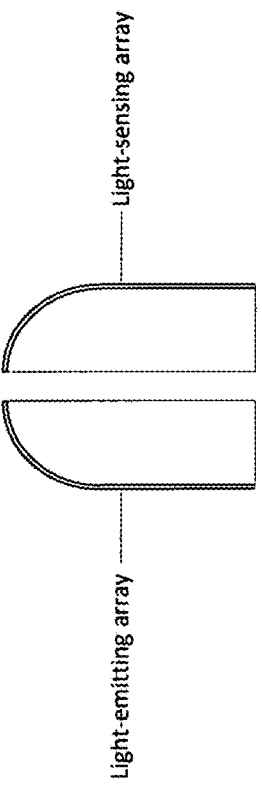
FIG. 46e illustrates the light emitting and sensing arrays of the holding module of FIG. 46d.
Figure 46D:
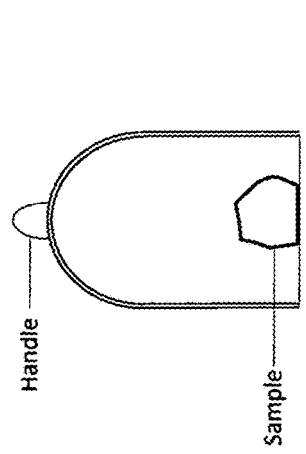
FIG. 46d illustrates an example holding module, as a bell configuration.
Figure 47B:
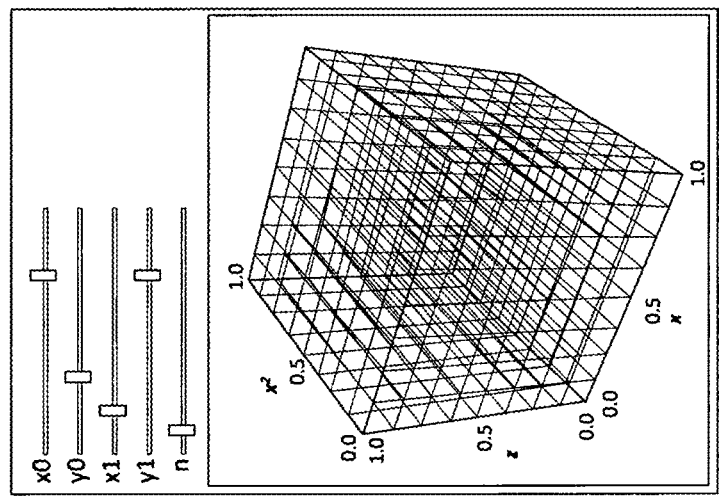
FIG. 47b shows an example graphical rendering in a visualizer module of a discretized three-dimensional space between a planar light emitting and light sensing arrangement.
Figure 47A:
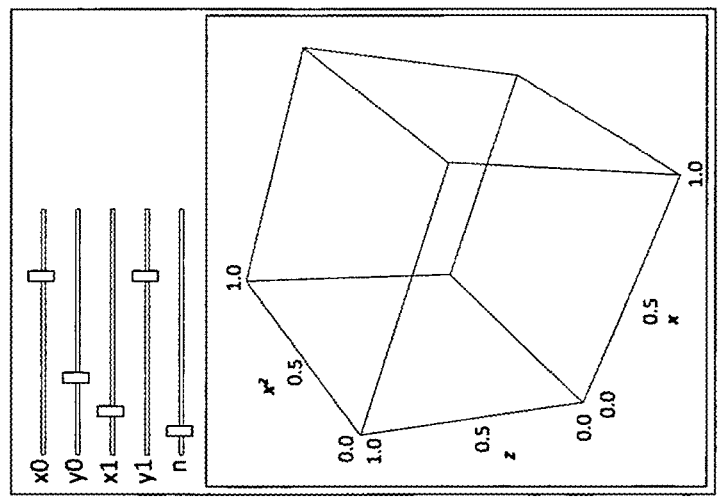
FIG. 47a shows an example graphical rendering in a visualizer module of three-dimensional space between a planar light emitting and light sensing arrangement.
Figure 48C:
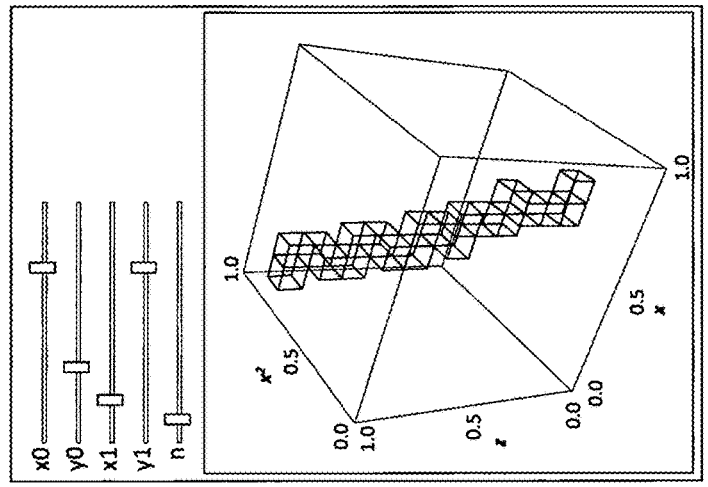
FIG. 48c further depicts an example graphical rendering in a visualizer module of an activation of discrete voxels intersected by the light path in discretized three-dimensional space.
Figure 48B:
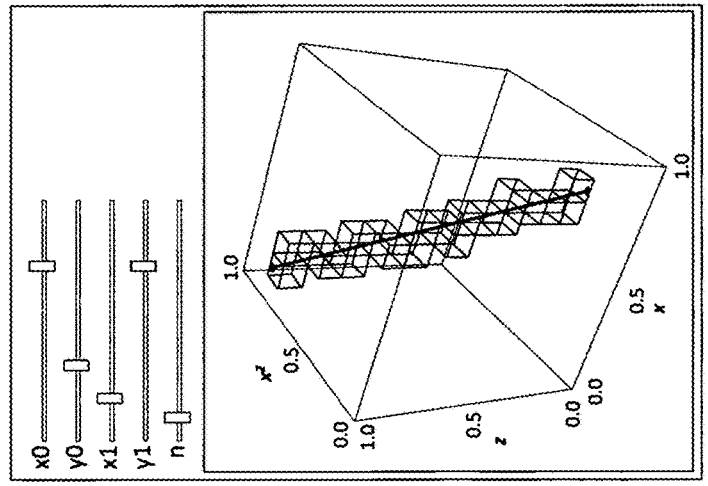
FIG. 48b depicts an example graphical rendering in a visualizer module of an activation of discrete voxels intersected by the light path in discretized three-dimensional space.
Figure 48A:
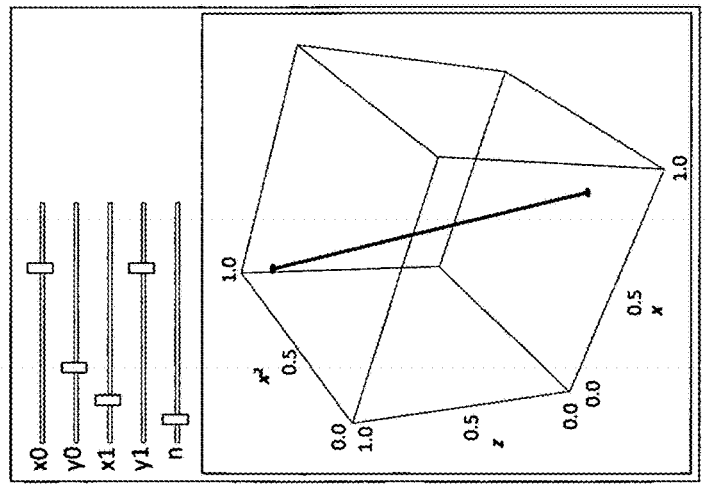
FIG. 48a depicts an example graphical rendering in a visualizer module of a light path between a light emission plane and a light sensing plane in three-dimensional space.
Figure 49B:
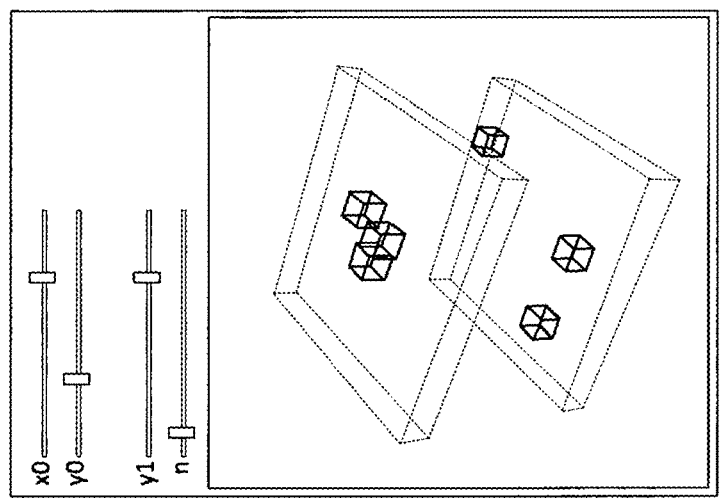
FIG. 49b depicts an example graphical rendering in a visualizer module of a cross-sectional view of a voxel arrangement in a discretized space.
Figure 49A:
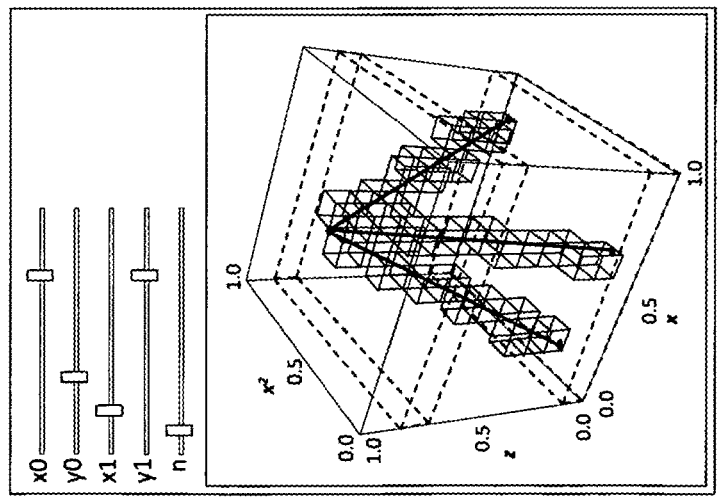
FIG. 49a depicts an example graphical rendering in a visualizer module of discretized planes in a discretized space, shown with voxels activated by multiple light paths.

FIG. 46d illustrates an example holding module, a comprising a "bell-jar"-like configuration. FIG. 46e illustrates the light emitting and sensing arrays of the holding module of FIG. 46d. In the case of the bell-shaped configuration, the light-emitting LEDs and light-sensing arrays can be arranged in such a way that one half of the bell comprising of light-emitting LEDs, and the other half comprising of light-sensing LEDs, as shown in this figure. In the form of a bell configuration, the arrangement can be placed over a sample.

The configurations of the holding modules can be adapted and combined in various ways depending on the application and size of the objects to be inserted. The holding modules can be made of various materials in order to optimize performance and maintain or improve the accuracy of measurements by the system.

7. Light-Path Visualizers

The present invention can further comprise a visualizer module to provide image viewing, editing, and processing capabilities for handling 3D data, voxel operations, local filtering, morphology, etc. The visualizer module can comprise various controls via a graphical user interface of the module, associated with varying the view and dimensions of the visual rendering. The visualization module can also include controls and sliders associated with mathematical properties of the visual rendering. FIGS. 47a, 47b, 48a, 48b, 48c, 49a, and 49b depict various example graphical renderings in a visualizer module. For example, as can be seen in FIGS. 47a, 47b, 48a, 48b, 48c, 49a, and 49b, coordinates associated with discretized space can be controlled via sliders on the top portion of a viewing window. Of course, the visualizer controls shown here are only example and can be modified depending on the functionality desired.

8. Example Applications

The present invention can be utilized in a variety of applications, such as in microscopy, microplates, fluorescence detection, microfluidics, cytometry, and flow cytometry. Other applications are anticipated and provided for by the invention.

8.1 Microscopy

Microscopy typically involves the use of optical microscopes and other related imaging systems in the study of small organisms, samples, and other objects that cannot be seen without magnification by the unaided eye. Microscopy has several branches, including for example optical microscopy and electron microscopy, each of which in turn have various sub-branches.

The present invention can be readily applied to the branch of optical microscopy, which images samples using properties of light. In the traditional sense, optical microscopes use a single or multiple lenses to magnify a sample so that it becomes visible to the naked eye.

Various embodiments of the present invention, as described, can be such that they do not use lenses. The invention, as applied to microscopy can image transparent samples. The resolution, determined by the size of the LEDs being used within the sensing and emitting arrays, also has potential to be high with the use of printed OLEDs (organic light-emitting diodes). Printed OLEDs are currently used to achieve the high-resolutions of television and smartphone screens, so it is entirely feasible to print OLEDs at fine resolution to recreate a high-resolution three-dimensional model of a microscopic object.

The invention's ability to three-dimensionally model an object will have very important applications in life sciences. Cells and cellular components, which are naturally transparent, can easily be imaged and modeled with the invention at very high-resolution. Currently there are similar microscopy technologies that also achieve three-dimensional modeling, including confocal microscopy, which also uses a scanning point of light. However, the cost of these technologies can be prohibitively high. The present invention has the potential to achieve the same resolution and same detailed three dimensional modeling at a much lower cost.

The ability to image a full three-dimensional model of a cell or organism can be invaluable when paired with fluorescence microscopy techniques. In fluorescent microscopy, fluorescent chemical compounds when combined with for example, antibodies, can be utilized as biological probes or to stain specific targets (i.e., cells, organelles, organisms, etc.) to be imaged for identifying the regions and structures within a cell or organism that have specific properties or chemical compositions.

It is understood that one skilled in the art can apply a different geometric configurations and/or other different arrangements to form alternate embodiments.

8.2 Fluorescence Detection Example

Figure 50:
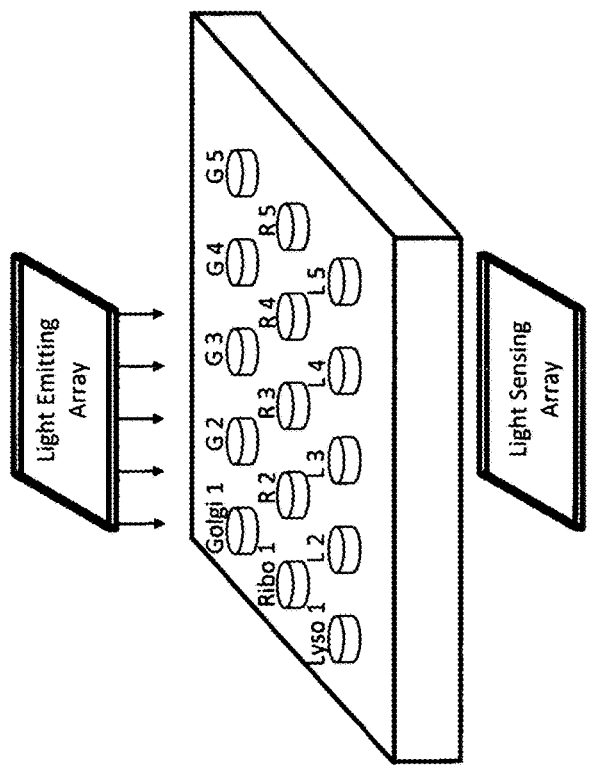
FIG. 50 depicts an example embodiment of a fluorescence detection application with a planar light emitting and light sensing arrangement in an optical tomography system.

One could also use fluorescence techniques to mark specific regions with a cell or organism and then use the invention to image, model, and locate the fluorescing regions. If ultraviolet (UV) excitation is utilized, to block unwanted effects of UV stimulation, a UV filter can also be applied to the invention. FIG. 50 depicts an example embodiment of a fluorescence detection application with a planar light emitting and light sensing arrangement in an optical tomography system. As shown in FIG. 50, varying types of target-specific fluorescent dyes can be applied to samples in the wells of a microplate. Specific organelles are recognized after their emitted fluorescent light is sensed. In this embodiment, a planar tomography configuration is depicted. Cylindrical and other arrangements for each well can also be applied.

It is understood that one skilled in the art can apply a different geometric configurations and/or other different arrangements to form alternate embodiments.

8.3 Cytometry and Flow Cytometry Example

Cytometry typically refers to the methods that are used to measure various characteristics of a cell, including cell size, current stage of the cell cycle, DNA content, and protein content. This is another very fitting application for the present invention. Cells are typically naturally transparent, making it very easy to derive a high-resolution three-dimensional model of the cell's interior contents and exterior membrane using our imaging techniques. This model can be used to accurately measure the three-dimensional shape of the cell, and can easily be examined determine the stage of the cell cycle. Again, fluorescent markers can be coupled with the invention to identify proteins and other chemicals within the cell. Similar to microscopy, the present invention can achieve ranges of microscopic resolution using printable OLEDs.

In one embodiment, the present application can also be applied to flow cytometry. Flow cytometry is the method of imaging cells as they move (or flow) in a liquid through the microscope. It is generally used for quickly amassing large amounts of data about a large number of cells. The invention could be adapted to allow for rapid imaging of moving objects to obtain high-resolution video-streams of cells.

Figure 51:
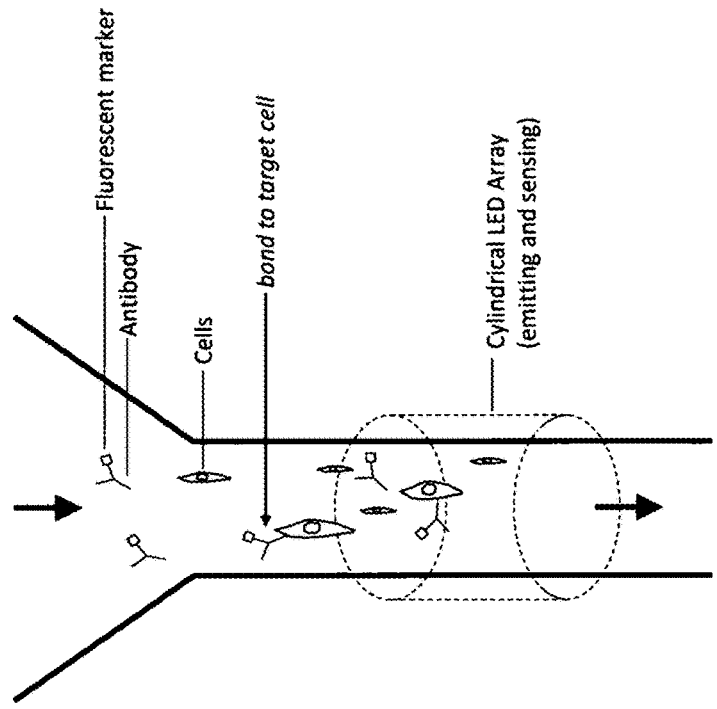
FIG. 51 depicts an example embodiment of a flow cytometry application with a cylindrical light emitting and light sensing arrangement in an optical tomography system.

FIG. 51 depicts an example embodiment of a flow cytometry application with a cylindrical light emitting and light sensing arrangement in an optical tomography system. Antibodies with fluorescent markers attach to specific target cells. Specific targets are recognized after light emitted from the fluorescent marker is sensed. Planar and other arrangements can also be applied.

It is understood that one skilled in the art can apply a different geometric configurations and/or other different arrangements to form alternate embodiments.

8.4 Microplate Example

Figure 52A:
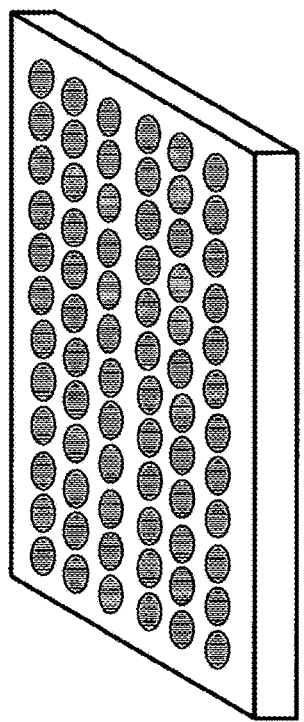
FIG. 52a illustrates an example embodiment of the present invention as a microplate.
Figure 52B:
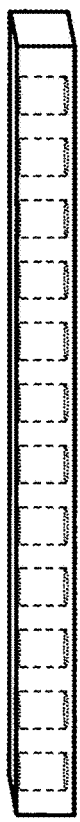
Figure 54:
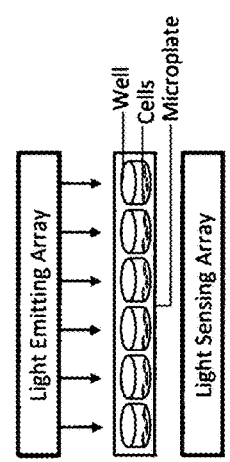
FIG. 54 depicts another example embodiment microplate with a planar light emitting and light sensing arrangement in an optical tomography system.
Figure 53:
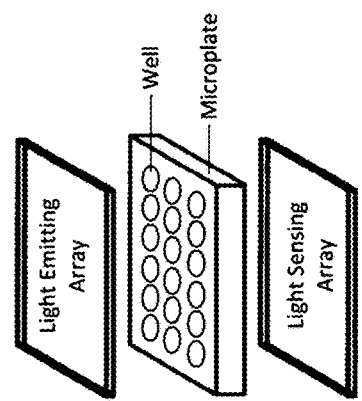
FIG. 53 depicts an example embodiment of a microplate with a planar light emitting and light sensing arrangement in an optical tomography system.

Microplates also provide a suitable application for the present application. In one embodiment, cylindrical geometry can be utilized in an embodiment of the present invention with microplates. FIG. 52*a* illustrates an example embodiment of the present invention as a microplate. FIG. 52*b* illustrates a side view of FIG. 52*a*. A cylindrical geometric arrangement of the present invention can be useful as implemented in individual wells of a microplate arrangement commonly used in chemical and life science settings. Such an application can provide a more powerful and detailed approach to imaging the sample within a well. In one embodiment, the light emitting and sensing arrays of the present application can be arranged with planar geometry as depicted in FIG. 52. FIG. 53 depicts an example embodiment of a microplate with a planar light emitting and light sensing arrangement in an optical tomography system. FIG. 54 depicts another example embodiment microplate with a planar light emitting and light sensing arrangement in an optical tomography system.

Figure 55A:
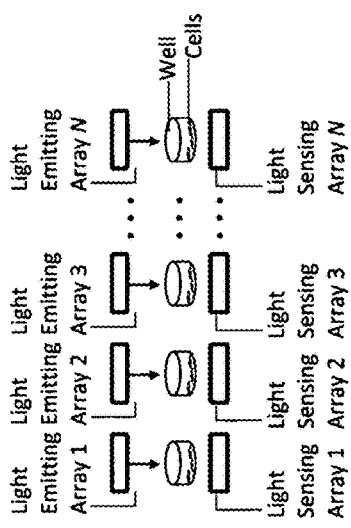
FIG. 55a depicts an example embodiment of a microplate with a planar light emitting and light sensing arrangement applied to each well of the microplate in an optical tomography system.

In another embodiment, a microplate with a planar light emitting and light sensing arrangement can be applied to each well of the microplate in an optical tomography system as depicted in FIG. 55*a*.

Figure 55B:
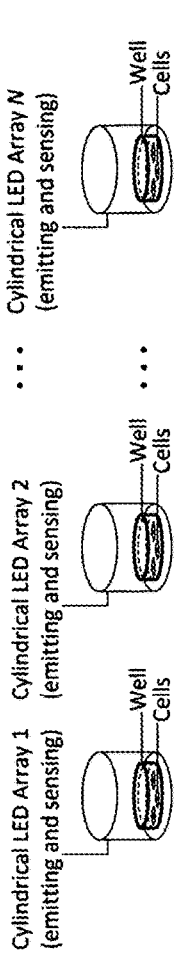
FIG. 55b depicts an example embodiment of a microplate with a cylindrical light emitting and light sensing arrangement applied to each well of the microplate in an optical tomography system.

In other embodiments, printing LEDs to form emitting and sensing arrays onto flexible and printable material could leverage the cylindrical geometry in the shape and scale of microplates. For example, FIG. 55*b* depicts an example embodiment of a microplate with a cylindrical light emitting and light sensing arrangement applied to each well of the microplate in an optical tomography system. Having a cylindrical arrangement can increase the angles from which the sample is scanned, as illustrated above generally for cylindrical arrangements.

It is understood that one skilled in the art can apply a different geometric configurations and/or other different arrangements to form alternate embodiments.

8.5 Culture Dish and Petri Dish Example

Figure 56A:
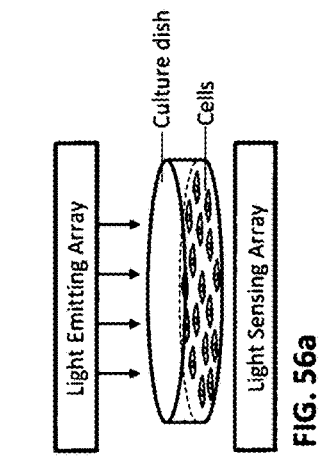
FIG. 56a depicts an example embodiment of a culture dish with a planar light emitting and light sensing arrangement in an optical tomography system.
Figure 56B:
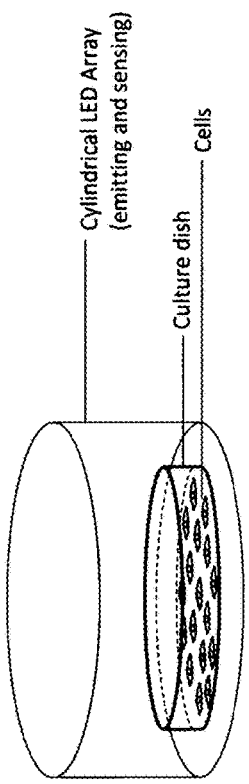
FIG. 56b depicts an example embodiment of a culture dish with a cylindrical light emitting and light sensing arrangement in an optical tomography system.

Either cylindrical or planar arrangements of the present application can also be applied to culture or Petri dishes commonly used in lab settings. For example, FIG. 56*a* depicts an example embodiment of a culture dish with a planar light emitting and light sensing arrangement in an optical tomography system. In yet another embodiment, FIG. 56*b* depicts an example embodiment of a culture dish with a cylindrical light emitting and light sensing arrangement in an optical tomography system.

It is understood that one skilled in the art can apply a different geometric configurations and/or other different arrangements to form alternate embodiments.

8.6 Microfluidic Example

Figure 57:
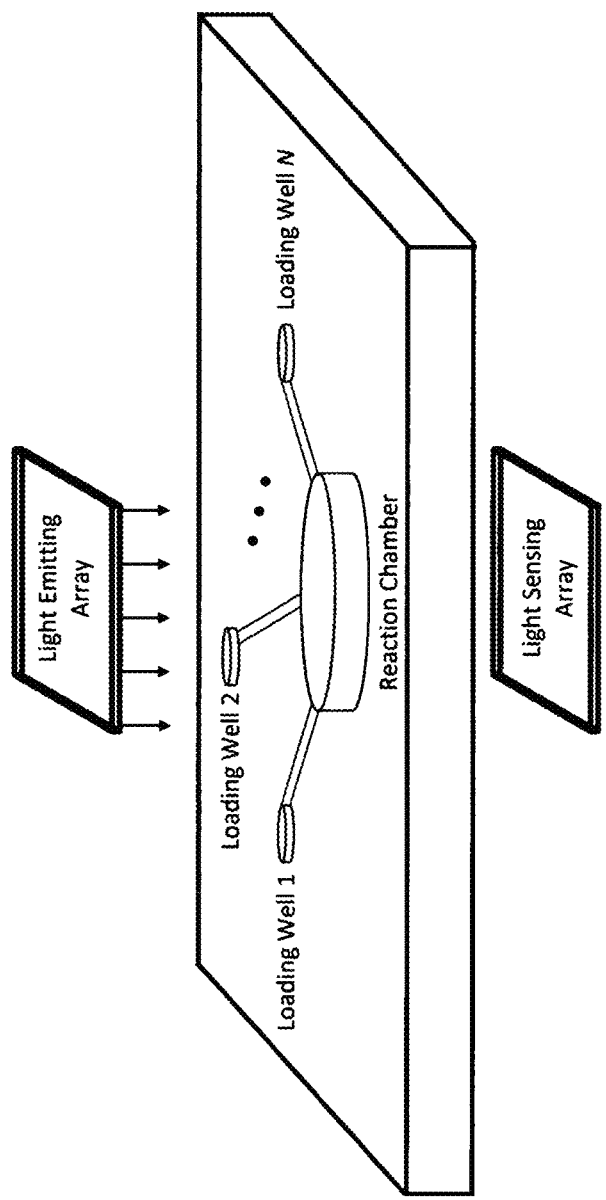
FIG. 57 depicts an example embodiment of a microfluidic plate with a planar light emitting and light sensing arrangement in an optical tomography system.

The present application also can be applied to microfluidic applications. As an example, FIG. 57 depicts an example microfluidic plate with a planar light emitting and light sensing arrangement in an optical tomography system. In FIG. 57, a planar geometry arrangement is applied to a reaction chamber on a microfluidic plate, used to detect reaction of substances in the reaction chamber.

It is understood that one skilled in the art can apply a different geometric configurations and/or other different arrangements to form alternate embodiments.

8.7 Incubation Chamber Example

Figure 58:
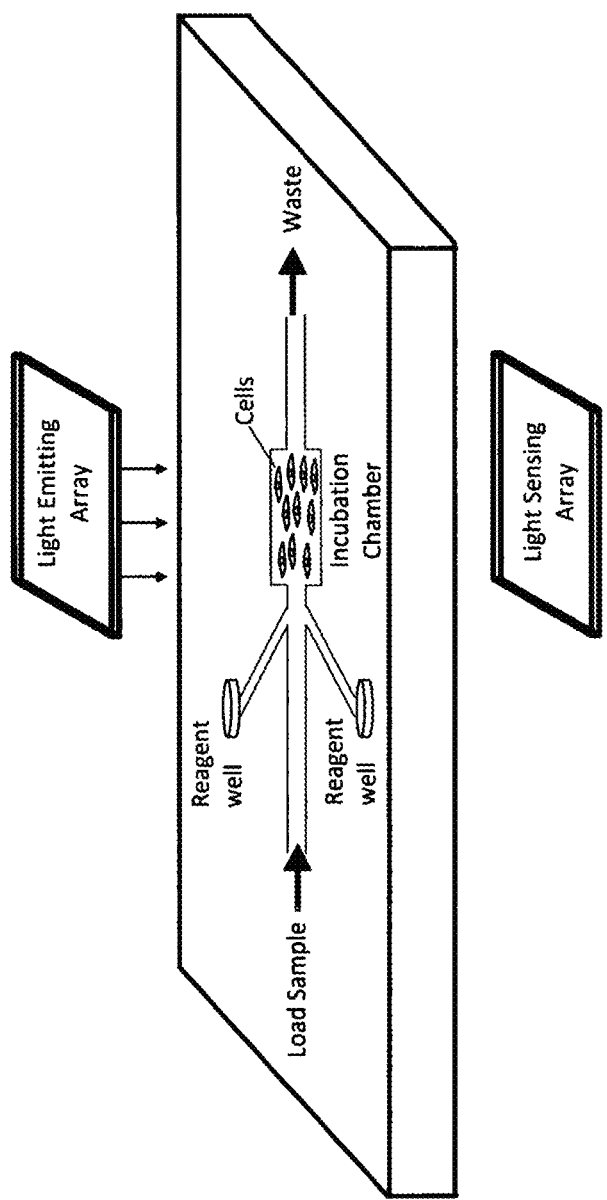
FIG. 58 depicts another example microfluidic plate with a planar light emitting and light sensing arrangement in an optical tomography system.

FIG. 58 depicts another example microfluidic plate with a planar light emitting and light sensing arrangement in an optical tomography system. FIG. 58 shows how the optical tomography system of the present application is used to scan the change in culture in a microfluidic incubation chamber. Although a planar configuration is applied to the microfluidic plate, other geometric arrangements can also be implemented.

In yet another embodiment, the present application can also be applied to a microfluidic structure or assembly found on lab-on-a-chip devices.

It is understood that one skilled in the art can apply a different geometric configurations and/or other different arrangements to form alternate embodiments.

8.8 Culture Chamber Example

Figure 59:
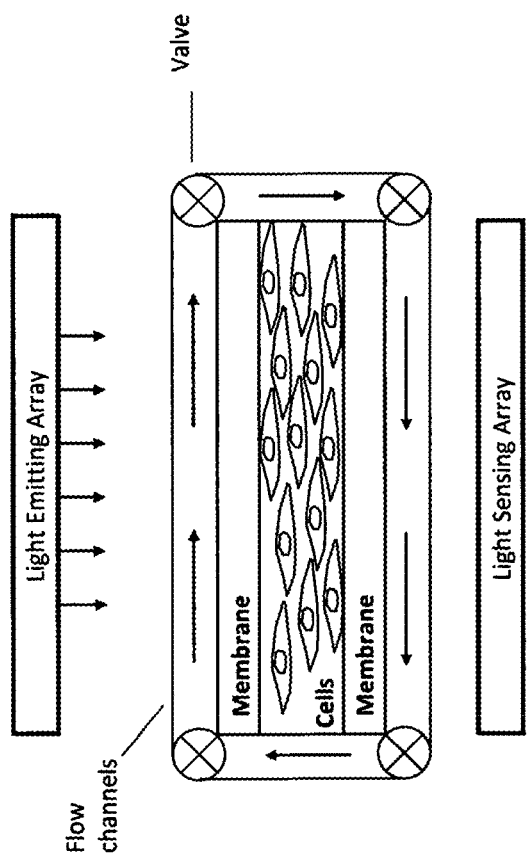
FIG. 59 depicts an example embodiment of a culture chamber, with a planar light emitting and light sensing arrangement in an optical tomography system.

Another biological application of the present application system is shown in FIG. 59, which depicts an example embodiment of a culture chamber, with a planar light emitting and light sensing arrangement in an optical tomography system. FIG. 59 shows the culture chamber enveloped in biological membranes that are selectively-permeable to media that flows through a channel surrounding them, wherein the present applications scans the culture chamber. This configuration can embody valves to control media flow.

It is understood that one skilled in the art can apply a different geometric configurations and/or other different arrangements to form alternate embodiments.

Closing

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

In addition, it will be appreciated that the various operations, processes, and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

Although example embodiments have been provided in detail, various changes, substitutions and alternations could be made thereto without departing from spirit and scope of the disclosed subject matter as defined by the appended claims. Variations described for the embodiments may be realized in any combination desirable for each particular application. Thus particular limitations and embodiment enhancements described herein, which may have particular advantages to a particular application, need not be used for all applications. Also, not all limitations need be implemented in methods, systems, and apparatuses including one or more concepts described with relation to the provided embodiments. Therefore, the invention properly is to be construed with reference to the claims.

The invention claimed is:

1. An optical tomography system comprising:
An illuminating light emitting array comprising a plurality of light emitting diodes (LEDs);
a sample holding module; and
a light sensing array comprising a plurality of light emitting diodes (LEDs),
wherein the light sensing array is configured to sense light emitted from the light emitting array after the light has passed through the sample holding module.

2. The optical tomography system of claim 1, wherein the plurality of light emitting diodes in the light emitting array are sequentially illuminated.

3. The optical tomography system of claim 1, wherein the illuminating LED array is configured, via sequencing, to operate both as a illuminating light source and as a reflective-imaging light sensor.

4. The optical tomography system of claim 1, wherein the illuminating LED array is configured, via multiplexing, to operate both as a illuminating light source and as a reflective-imaging light sensor.

5. The optical tomography system of claim 1, wherein at least one of the LEDs in the illuminating light emitting array is an organic light emitting diode (OLED).

6. The optical tomography system of claim 1, wherein at least one of the LEDs in the light sensing array is an organic light emitting diode (OLED).

7. The optical tomography system of claim 1, wherein the illuminating light emitting array is planar array.

8. The optical tomography system of claim 1, wherein the light sensing array is a planar array.

9. The optical tomography system of claim 1, wherein the illuminating light emitting non-array is planar array.

10. The optical tomography system of claim 1, wherein the light sensing array is a non-planar array.

11. The optical tomography system of claim 1, wherein the system is configured to provide an over-specified system of equations relating light-adsorption voxel values to light measurement values.

12. The optical tomography system of claim 11, wherein the over-specified system of equations is linearized via the use of logarithm operations to produce a linearized over-specified system of equations.

13. The optical tomography system of claim 12, wherein the linearized over-specified system of equations is solved for logarithms of approximate light-adsorption voxel values using a generalized inverse operation.

14. The optical tomography system of claim 1, wherein the sample module accepts a microscope slide.

15. The optical tomography system of claim 1, wherein the sample module accepts a microscope slide.

16. The optical tomography system of claim 1, wherein the sample module accepts a microscope slide.

17. The optical tomography system of claim 1, wherein the sample module is cylindrical.

18. The optical tomography system of claim 1, wherein the sample module is spherical.

\* \* \* \* \*

UNITED STATES PATENT AND TRADEMARK OFFICE
CERTIFICATE OF CORRECTION

| | | |
|---|---|---|
| PATENT NO. | : 9,594,019 B1 | Page 1 of 1 |
| APPLICATION NO. | : 13/963931 | |
| DATED | : March 14, 2017 | |
| INVENTOR(S) | : Lester F. Ludwig | |

It is certified that error appears in the above-identified patent and that said Letters Patent is hereby corrected as shown below:

In the Claims

Column 26, Line 52 Claim 3 "a illuminating" should read --an illuminating--.

Column 26, Line 56 Claim 4 "a illuminating" should read --an illuminating--.

Column 27, Line 2 Claim 9 "non-array" should read --array--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*